United States Patent [19]
El-Rashidy et al.

[11] Patent Number: 5,994,363
[45] Date of Patent: Nov. 30, 1999

[54] AMELIORATION OF APOMORPHINE ADVERSE EFFECTS

[75] Inventors: Ragab El-Rashidy, Deerfield; Bruce Ronsen, River Forest, both of Ill.

[73] Assignee: Pentech Pharmaceuticals, Inc., Buffalo Grove, Ill.

[21] Appl. No.: 09/138,982

[22] Filed: Aug. 24, 1998

[51] Int. Cl.$^6$ .................................................. A61K 31/44
[52] U.S. Cl. ............................................................ 514/284
[58] Field of Search ............................................. 514/284

[56] References Cited

U.S. PATENT DOCUMENTS

| | | | |
|---|---|---|---|
| 2,818,855 | 1/1958 | Miller . | |
| 3,976,780 | 8/1976 | Thominet | 424/27 S |
| 4,127,118 | 11/1978 | Latorre . | |
| 4,521,421 | 6/1985 | Foreman . | |
| 4,543,256 | 9/1985 | Neumeyer . | |
| 4,569,940 | 2/1986 | Watts | 514/304 |
| 4,624,965 | 11/1986 | Wenig | 514/619 |
| 4,687,773 | 8/1987 | Neumeyer et al. . | |
| 4,749,686 | 6/1988 | Hintze | 514/12 |
| 4,749,700 | 6/1988 | Wenig | 514/225.2 |
| 4,772,459 | 9/1988 | Sun et al. | 424/10 |
| 4,801,587 | 1/1989 | Voss . | |
| 5,102,887 | 4/1992 | Goldberg | 514/282 |
| 5,242,391 | 9/1993 | Place et al. . | |
| 5,270,323 | 12/1993 | Milne, Jr. et al. . | |
| 5,310,561 | 5/1994 | Jao et al. | 424/465 |

OTHER PUBLICATIONS

Danjou et al., Br. J. Clin. Pharmac. 26:733–739 (1988).
Gancher et al., Ann. Neurol. 26:232–238 (1989).
Segraves, Arch. Gen. Psych. 46:275–284 (1989).
Heaton et al., J. Urology 145:1099–1102 (1991).
Montastruc et al., Clin. Neuropharmacology 14(5):432–437 (1991).
Durif et al., Eur. J. Clin. Pharmacology 41:493–494 (1991).
Gancher et al., Movement Disorders 6(3):212–216 (1991).
Segraves et al., J. Urology 145:1174–1175 (1991).
Segraves, R.T., Dopamine agonists and their effect on the human penile erectile response, pp. 225–229 in Bancroft, J., editor, *The Pharmacology of Sexual Function and Dysfunction,* Excerpta Medica, Amsterdam (1995).

*Primary Examiner*—James H. Reamer
*Attorney, Agent, or Firm*—Olson & Hierl, Ltd.

[57] ABSTRACT

Symptoms of Parkinson's disease and psychogenic male erectile dysfunction (MED) can be ameliorated through the use of apomorphine. The adverse side effects of apomorphine administration, such as nausea, vomiting, yawning, and cardiovascular effects, can be significantly reduced by a dose escalating method of acclimatization. An initial dose of apomorphine is administered to the patient, and subsequently increased over a period of time until a final apomorphine dose in excess of a desired therapeutic dose has been received by the patient. Thereafter a therapeutic dose of apomorphine, less than the final apomorphine dose, is administered to the patient with attendant reduced side effects.

23 Claims, 17 Drawing Sheets

SEXUAL FUNCTION STUDY HOME QUESTIONNAIRE - Male
Please answer questions within 12-24 hours of taking sublingual tablet.

Initials:_____ Subject #:_____     Today's Date:_____Time:_____

Date Tablet Taken:_____Time:_____

The lines below represent the full range of feeling or response. Please mark each line clearly with a vertical (straight up and down) stroke at the point which represents your response. (There are no right or wrong answers. Do not write in boxes on right.)

1. What was your erection result after taking the sublingual tablet?

*No Erection* ——————————————————— *Rigid Erection Suitable for Penetration*

2. Did you have intercourse with wife/partner after taking tablet?     [ ] Yes     [ ] No IF NO, please circle all reasons that apply:
0-No erection.
1-Erection not sufficient for penetration.
2-Felt sick after taking tablet.(Describe below in #4.)
3-I decided not to participate in intercourse.
4-Wife/partner decided not to participate.
5-Unrelated interruption (example, telephone call).
6-Wife/partner menstruating.
7-Other, explain:_____

3. What was your level of satisfaction with this attempt at sexual intercourse?

*Extremely Unsatisfied* ——————————————————— *Extremely Satisfied*

4. Please describe any adverse reactions you experienced after taking the sublingual tablet. (Indicate when the reaction started and stopped, and any intervention taken i.e. "nosebleed on 5/1/94, used a cold compress".)

_____
_____
_____

5. Other comments?_____
_____

FIG. 15

SEXUAL FUNCTION STUDY HOME QUESTIONNAIRE - Female
Please answer questions within 12-24 hours of taking sublingual tablet.

Initials:_____ Subject #:_____     Today's Date:_____Time:_____

Date Tablet Taken:_____Time:_____

The lines below represent the full range of feeling or response. Please mark each line clearly with a vertical (straight up and down) stroke at the point which represents your response. (There are no right or wrong answers. Do not write in boxes on right.)

1. What was your husband's/partner's erection result after taking the sublingual tablet?

No Erection ———————————————————— Rigid Erection Suitable for Penetration

2. Did you have intercourse with      [ ] Yes      [ ] No
   husband/partner after taking tablet?

IF NO, please circle
all reasons that apply:
- 0-No erection.
- 1-Erection not sufficient for penetration.
- 2-Husband/partner was ill after taking tablet.
- 3-I decided not to participate in intercourse.
- 4-Husband/partner decided not to participate.
- 5-Unrelated interruption (example, telephone call).
- 6-Menstruating.
- 7-Other, explain:_____

3. What was your level of satisfaction with this attempt at sexual intercourse?

Extremely Unsatisfied ———————————————————— Extremely Satisfied

4. Other comments?_____
_____
_____

FIG. 16

Visual Analogue Scale (VAS)
(to be completed by the patient)

*Please mark each line clearly at the point which indicates how you are feeling right now. Each line represents the full range of each feeling. (There are no right or wrong answers)*

|     |                 |     |              | Score (mm) |
|-----|-----------------|-----|--------------|------------|
| 1.  | Alert           | ——— | Drowsy       | ____       |
| 2.  | Calm            | ——— | Excited      | ____       |
| 3.  | Yawning         | ——— | Not Yawning  | ____       |
| 4.  | Fuzzy           | ——— | Clear Headed | ____       |
| 5.  | Well Coordinated| ——— | Clumsy       | ____       |
| 6.  | Tired           | ——— | Energetic    | ____       |
| 7.  | Contented       | ——— | Disconnected | ____       |
| 8.  | Troubled        | ——— | Tranquil     | ____       |
| 9.  | Mentally slow   | ——— | Quick Witted | ____       |
| 10. | Tense           | ——— | Relaxed      | ____       |
| 11. | Attentive       | ——— | Dreamy       | ____       |
| 12. | Stomach Upset   | ——— | Feeling Well | ____       |
| 13. | Anxious         | ——— | Carefree     | ____       |

(measure from left to right)

FIG. 17

AMELIORATION OF APOMORPHINE ADVERSE EFFECTS

TECHNICAL FIELD

This invention relates to amelioration of the adverse effects, such as nausea, yawning, vomiting, and cardiovascular effects, caused to human patients when taking apomorphine for Parkinson's disease, psychogenic male erectile dysfunction (MED), and female sexual dysfunction, or the like afflictions.

BACKGROUND OF THE INVENTION

Apomorphine has been used to treat Parkinsonian patients. See, for example, Deffond et al., J. Neurology, Neurosurgery, and Psychiatry 56:101–103 (1993) and Durif et al., Clinical Neuropharmacology 16(2):157–166 (1993). Additionally, apomorphine has been considered for the treatment of alcoholism, schizophrenia, dystonia musculorum deformans, hallucinations, migraine headaches, hiccups, Huntington's chorea, tardative dyskinesia, and more recently male erectile dysfunction.

Administration of large doses of apomorphine to mammals such as humans, dogs and the like usually results in nausea and vomiting, and is believed to be due to the action of apomorphine on the chemoreceptor trigger zone (CTZ) of the medulla oblongata, a structure of the mammalian central nervous system. It is also believed that additional chemoreceptors triggering emesis are present in the gastrointestinal tract as well.

Impotence or male erectile dysfunction is defined as the inability to achieve and sustain an erection sufficient for intercourse. Impotence in any given case can result from psychological disturbances (psychogenic), from physiological abnormalities in general (organic), from neurological disturbances (neurogenic), hormonal deficiencies (endocrine) or from a combination of the foregoing.

These descriptions are not exact, however. There is currently no standardized method of diagnosis or treatment. As used herein, psychogenic impotence is defined as functional impotence with no apparent overwhelming organic basis. It may be characterized by an ability to have an erection in response to some stimuli (e.g., masturbation, spontaneous nocturnal, spontaneous early morning, video erotica, etc.) but not others (e.g., partner or spousal attention).

The effect of apomorphine on penile tumescence in male patients afflicted with psychogenic impotence has also been studied. These studies show that while apomorphine can indeed induce an erection in a psychogenic male patient, the apomorphine dose required to achieve a significant erectile response is usually accompanied by nausea or other serious undesirable side effects, including hypertension, flushing and diaphoresis (sweating). The specific mechanisms by which apomorphine acts to produce an erectile response in a human patient are not yet completely understood, however.

Moreover, apomorphine has been shown to have very poor oral bioavailability. See, for example, Baldessarini et al., in Gessa et al., eds., *Apomorphine and Other Dopaminomimetics, Basic Pharmacology*, Vol. 1, Raven Press, N.Y. (1981), pp. 219–228. Thus the search is continuing for an effective treatment of psychogenic impotence in male patients as well as for diagnostic methods that can identify such patients.

It has now been found that certain delivery systems for apomorphine can provide a practical therapeutic and/or diagnostic "window" while reducing the likelihood of undesirable side effects.

Acute and subacute testing of apomorphine HCl has been reported in studies with daily doses ranging to over 300 milligrams per kilogram (mg/kg) in lower vertebrates (amphibian and birds), and to 10 mg/kg in higher mammals (primates). In mammals, it appears doses of apomorphine HCl are tolerated up to about 13 mg/kg in a single bolus subcutaneous injection. Doses at or above this amount have been reported lethal in mouse, although, the LD50 is considerably higher (>50 mg/kg) in this species. Continuous infusion of apomorphine has been tolerated and reported to doses of 420 $\mu$g/kg/hr for 14 days. Larger doses (1,500 $\mu$g/kg/hr were found to be minimally lethal over the course of the 14 day study). In primates, multiple doses of apomorphine HCl have been administered for up to four days at 100–400 $\mu$g/kg without major adverse effects.

However, in 1995, *The Pharmacology of Sexual Function and Dysfunction* (J. Bancroft, editor), in an article at pp. 225–229 entitled "Dopamine agonists and their effect on the human penile erectile response" by R. T. Segraves, M.D., summarized evidence concerning the use of dopamine agonists especially apomorphine to induce erectile responses in human males. The article concludes that "[c]learly, apomorphine has too many side effects to have therapeutic usefulness."

Notwithstanding the Segraves article, apomorphine dosage forms have been found to be effective in treating Parkinson's disease as well as in male patients suffering from psychogenic erectile dysfunction for the induction and maintenance of an erection sufficient for intercourse (i.e., vaginal penetration). While at relatively lower dosages apomorphine can be administered without nausea or other undesirable side effects, such side effects do manifest themselves as the dosages of apomorphine are increased.

When the plasma concentration of apomorphine is maintained at no more than about 5.5 nanograms per milliliter (ng/ml), the incidence of adverse side effects is minimal. Such monitoring, of course, requires either an invasive procedure, such as blood analysis or urinalysis, to determine proper dosing requirements.

The present method provides for the amelioration of adverse effects due to apomorphine use without the invasiveness of previous methods.

SUMMARY OF THE INVENTION

Adverse effects of apomorphine, such as nausea, vomiting, yawning, cardiovascular effects, etc., on a human patient are minimized by administration of an escalating dosage of apomorphine over a period of time. The method begins with the administering of a threshold or initial dose of apomorphine, followed by periodic increasing doses of apomorphine until a final dose in excess of a therapeutic dose is administered. A therapeutic dose of apomorphine is then administered to the patient for purposes of treatment.

In a preferred embodiment for treating psychogenic impotence sublingual doses of apomorphine are administered periodically. The final dose of apomorphine is preferably in excess of that needed to produce a sufficiently rigid erection in the patient. The therapeutic sublingual dose is less than the final dose of apomorphine but still sufficient to produce an erection with sufficient rigidity for vaginal penetration without the attendant substantial adverse effects. Preferably, the sublingual threshold dose of apomorphine for a human patient can be in the range of about 2 to about 8 milligrams (mg), and more preferably about 4 mg. The increased dosing occurs preferably at a rate of about 2 mg each day for a period of no less than three days, with the therapeutic dose of apomorphine administered after the final dose is given. The final dose of apomorphine administered to a human patient suffering from psychogenic erectile dysfunction is about 8 to 10 mg. The sublingual therapeutic dose of apomorphine is preferably 6 mg, and can vary, depending upon the patient in the range of about 35 to about 74 micrograms per kilogram (µg/kg) of the patient's body weight, and most preferably within the range of about 50 to about 74 micrograms per kilogram (µg/kg) of body weight.

For patients with Parkinson's disease, a subcutaneous therapeutic dose, i.e. sufficient to ameliorate Parkinsonism symptoms, can be as high as about 8 mg, usually about 3–5 mg, per administration. A sublingual therapeutic dose for treating Parkinsonism symptoms can be as high as about 60 mg, usually about 20 to about 40 mg. Subcutaneous threshold doses can be in the range of about 1.25 mg to about 5 mg, usually about 3 mg. Nothwithstanding dosage form, the plasma concentration of apomorphine is preferably maintained in the range of about 3 to about 20 nanograms per milliliter for treatment of Parkinsonism symptoms.

For patients with female sexual dysfunction, administration of apomorphine to females has been shown to increases nerve stimulated clitoral intracavernosal blood flow and vaginal wall blood flow, each of which is associated respectively with enhanced clitoral erection and vaginal engorgement in a female.

A sublingual apomorphine dosage form, usually containing about 2 to about 12 mg, preferably about 2 to about 8 mg, of apomorphine, is effective for producing sexual readiness in human females without inducing substantial nausea or other undesirable side effects. Sublingually, administration is effected preferably about 15 to about 20 minutes prior to sexual activity. The plasma concentration of apomorphine is maintained at no more than about 5.5 ng/ml, preferably about 0.3 to about 4 ng/ml, and more preferably about 1 to about 2 ng/ml, to maintain a circulating serum level and mid-brain tissue level of apomorphine during the period of sexual activity sufficient to maintain vaginal engorgement, its associated lubrication and clitoral erection during coitus.

For patients diagnosed with social phobia, a dopaminergic agonist such as apomorphine reduces the patient's inability to engage in social interactions that characterizes social phobia. Treatment regimens that achieve a target plasma concentration of apomorphine in the range of about 0.5 ng/ml to about 10 ng/ml at $C_{max}$ with chronic therapy of 2 or more treatments provide a therapeutically effective dose that produces amelioration of social phobia in a patient.

BRIEF DESCRIPTION OF THE DRAWING

In the drawings,

FIG. 15 represents a sample sexual function study home questionnaire for the male participant, which required completion within about 12 to about 24 hours after administering a sublingual dose of apomorphine;

FIG. 16 represents a sample sexual function study home questionnaire for the female partner of the male participant, which required completion within about 12 to about 24 hours after administration of sublingual dose of apomorphine; and FIG. 17 represents a sample Visual Analogue Scale questionnaire used to determine the patient's sense of well being, level of sedation, tranquilization, anxiousness, arousal and any changes in yawning behavior.

DESCRIPTION OF THE PREFERRED EMBODIMENT

Figure 1:
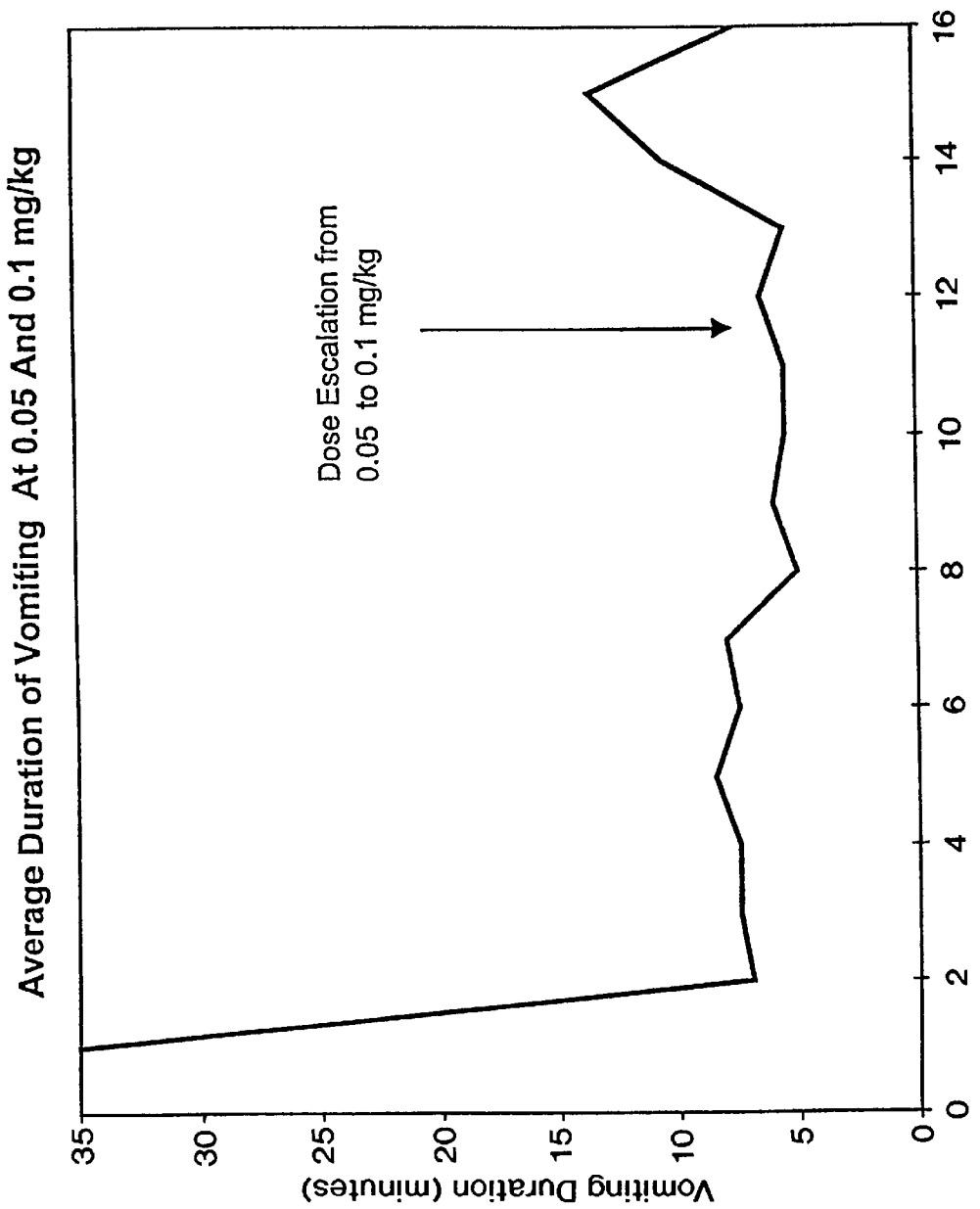
FIG. 1 is a plot of duration of nausea/retching and vomiting versus time for dogs at an apomorphine acclimatization dose of 0.05 mg/kg.

While the present invention is susceptible to embodiments in many different forms, a preferred embodiment of the invention is described below. It should be understood, however, that the present disclosure is to be considered as an exemplification of the principles of the invention and is not intended to limit the invention to the specific embodiments illustrated.

Apomorphine is a dopamine receptor agonist that has a recognized use as an emetic when administered subcutaneously in about a 5-milligram dose. For the purposes of the present invention, apomorphine is administered in an amount sufficient to excite cells in the mid-brain region of a patient. This cell excitation is believed to be part of a cascade of stimulation that is likely to include neurotransmission with serotonin and oxytocin.

The dopamine receptors in the mid-brain region of a patient can be stimulated to a degree sufficient to cause an erection by the sublingual administration of apomorphine. Apomorphine, also known by the chemical name (R)-5,6,6a,7-Tetrahydro-6-methyl-4H-dibenzo-[de,g] quinoline-10,11-diol, has the following chemical structure:

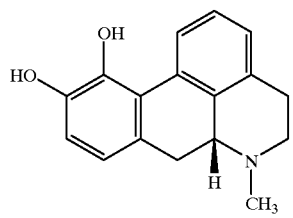

The sublingual administration usually takes place over a time period in the range of about 2 to about 10 minutes, or longer. The amount of apomorphine administered sublingually over this time period preferably is in the range of about 35 to about 74 micrograms per kilogram ($\mu$g/kg) of the patient's body weight, and most preferably within the range of about 50 to about 74 $\mu$g/kg of body weight.

Acclimatization to the usual side effects resulting from chronic administration of apomorphine can be achieved using a regimen and route where the patient is conditioned to the drug via blood levels where the drug is at or about at the plasma concentration likely to produce these effects. Administration of apomorphine for acclimatization may take the form of parenteral, oral or sublingual routes of administration. The sublingual route is preferred for patients suffering from psychogenic erectile dysfunction.

For rapid acclimatization, a customized, responsive regimen is preferred. The therapeutic dose is preferably identified as the smallest dose of apomorphine at which the patient experiences related adverse effects. The threshold dose is repeated until no unacceptable side effects are found. The frequency of repeated apomorphine administrations may vary, but is preferably in the range of about 1 day to about 1 week per administration.

Next, the apomorphine dose is increased until adverse effects are again experienced. Administration of the increased dosage is now repeated until the patient no longer experiences adverse effects. For escalation of subsequent doses the previously tolerated dose preferably is doubled. The dosage escalation is repeated until the dosage level of apomorphine exceeds the therapeutic dose for the target medical condition.

Illustrative acclimatization schedules are presented in Table Ia, below.

For more convenient distribution and mass administration, a more structured acclimatization regimen is preferred. In one embodiment of the present invention for treating psychogenic, impotence sublingual doses of apomorphine are administered according to the acclimatization regimen presented in Table Ib.

TABLE Ib

Impotence Treatment-Dose Schedule For Apomorphine Acclimatization

| Day | Threshold Dose (Week 1) | Increased Dose (Week 2) | Final Dose (Week 3) | Therapeutic Dose[1] (Week 4) |
|---|---|---|---|---|
| 1 | 2 mg tablet | 3 mg tablet | 4 mg tablet | therapeutic tablet |
| 2 | 2 mg tablet | 3 mg tablet | 4 mg tablet | therapeutic tablet |
| 3 | 2 mg tablet | 3 mg tablet | 4 mg tablet | therapeutic tablet |
| 4 | 2 mg tablet | 3 mg tablet | 4 mg tablet | therapeutic tablet |
| 5 | 2 mg tablet | 3 mg tablet | 4 mg tablet | therapeutic tablet |
| 6 | 2 mg tablet | 3 mg tablet | 4 mg tablet | therapeutic tablet |
| 7 | 2 mg tablet | 3 mg tablet | 4 mg tablet | therapeutic tablet |

The 2-mg tablet called for during week 1 has been found to be a threshold dose for most impotence patients. The therapeutic sublingual dose called for in week 4 is less than the final dose of apomorphine but still sufficient to produce an erection with sufficient rigidity for vaginal penetration. Without violating this constraint, the therapeutic dose may vary by patient.

Table Ic, below, represents an acclimatization regimen for treating Parkinsonism symptoms.

TABLE Ic

Parkinsonism Symptoms Treatment-Dose Schedule For Apomorphine Acclimatization

| Day | Threshold Dose (Week 1) | Increased Dose (Week 2) | Final Dose (Week 3) | Therapeutic Dose[1] (Week 4) |
|---|---|---|---|---|
| 1 | 20 mg tablet | 30 mg tablet | 40 mg tablet | therapeutic tablet |
| 2 | 20 mg tablet | 30 mg tablet | 40 mg tablet | therapeutic tablet |
| 3 | 20 mg tablet | 30 mg tablet | 40 mg tablet | therapeutic tablet |
| 4 | 20 mg tablet | 30 mg tablet | 40 mg tablet | therapeutic tablet |
| 5 | 20 mg tablet | 30 mg tablet | 40 mg tablet | therapeutic tablet |
| 6 | 20 mg tablet | 30 mg tablet | 40 mg tablet | therapeutic tablet |
| 7 | 20 mg tablet | 30 mg tablet | 40 mg tablet | therapeutic tablet |

TABLE Ia

Dose Schedule For Apomorphine Acclimatization

| Plasma[1] Concentration Range(ng/ml) | Threshold or Initial Dose | Final Dose | Frequency[2] | Route | Uses |
|---|---|---|---|---|---|
| 0.25–4.0 | 2 mg tablet | 6 mg tablet | 1 per day | sublingual | sexual dysfunction |
| 3.0–25 | 0.25 mg | 3.0 mg | 1 per week | subcutaneous | Parkinson's disease |
| 4.0–30 | 8 mg tablet | 40 mg tablet | 1 per day | sublingual | Parkinson's disease |

Notes:
[1]Plasma Range is the therapeutic target and based on the Therapeutic $C_{max}$ in nanograms of apomorphine per milliliter of plasma.
[2]The frequencies are average intervals between the given doses. A higher frequency is desirable in routes where the plasma concentration is shorter lived, e.g. subcutaneous or continuous infusion. Hourly doses can be administrated for patients requiring very high plasma concentrations of apomorphine, such as in Parkinson's disease.

The therapeutic sublingual dose called for in week 4 is less than the final dose of apomorphine but still sufficient to substantially reduce Parkinsonism symptoms.

The structured acclimatization regimens presented in Tables Ib and Ic have advantages for patient acceptance and compliance. The necessary sublingual tablets can be arranged in a calendar-card tablet dispenser.

Animal Studies

This invention is illustrated further by the following examples.

EXAMPLE 1

Figure 2:
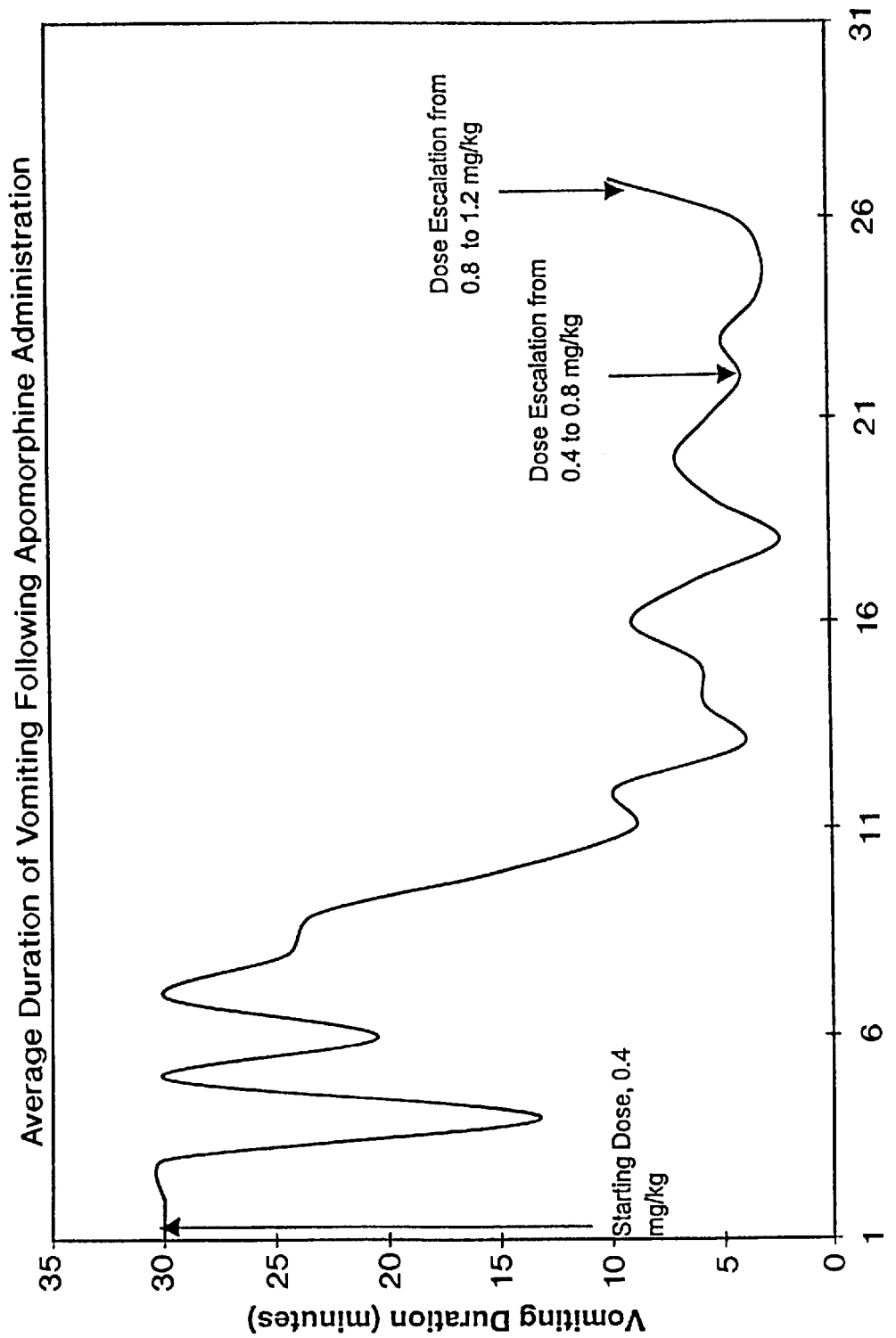
FIG. 2 is a plot of duration of nausea/retching and vomiting versus time for dogs at an apomorphine acclimatization dose of 0.4 mg/kg.
Figure 3:
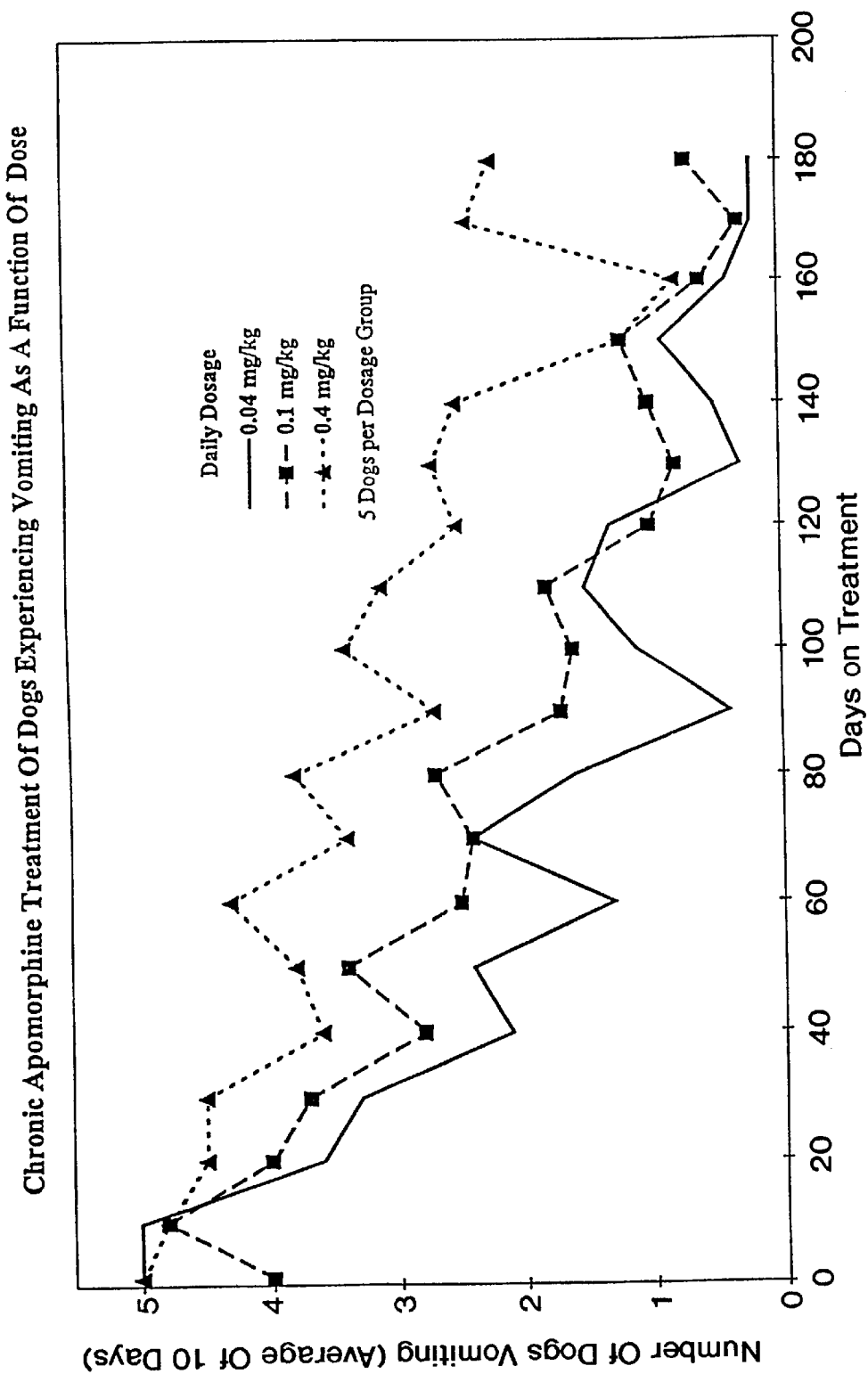
FIG. 3 is a plot over several days of number of dogs experiencing vomiting in the first five minutes following apomorphine administration at three different dosages of apomorphine.
Figure 4:
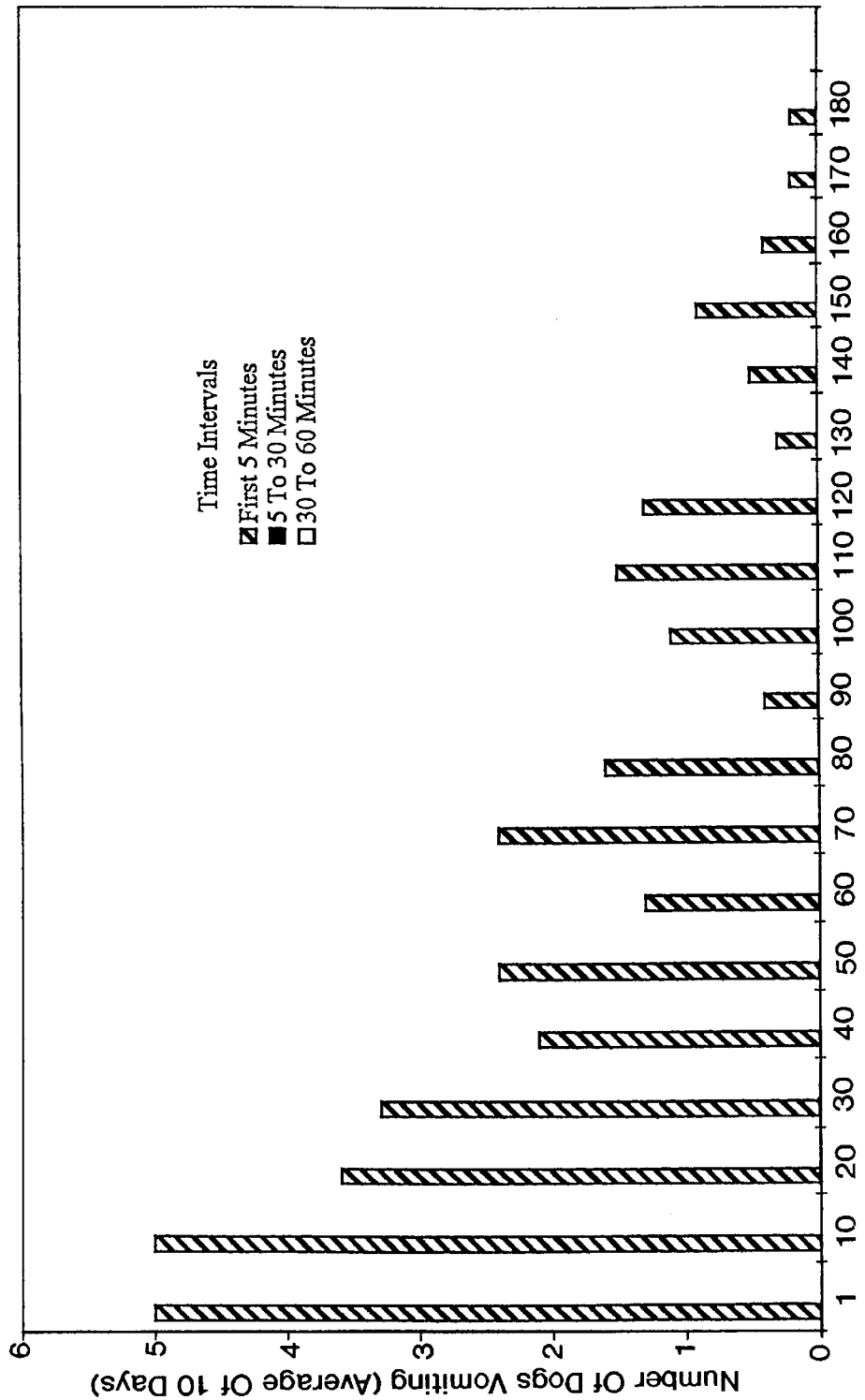
FIG. 4 is a plot over several days of number of dogs experiencing vomiting within three time periods following administration of 0.04 mg apomorphine per kg dog.
Figure 5:
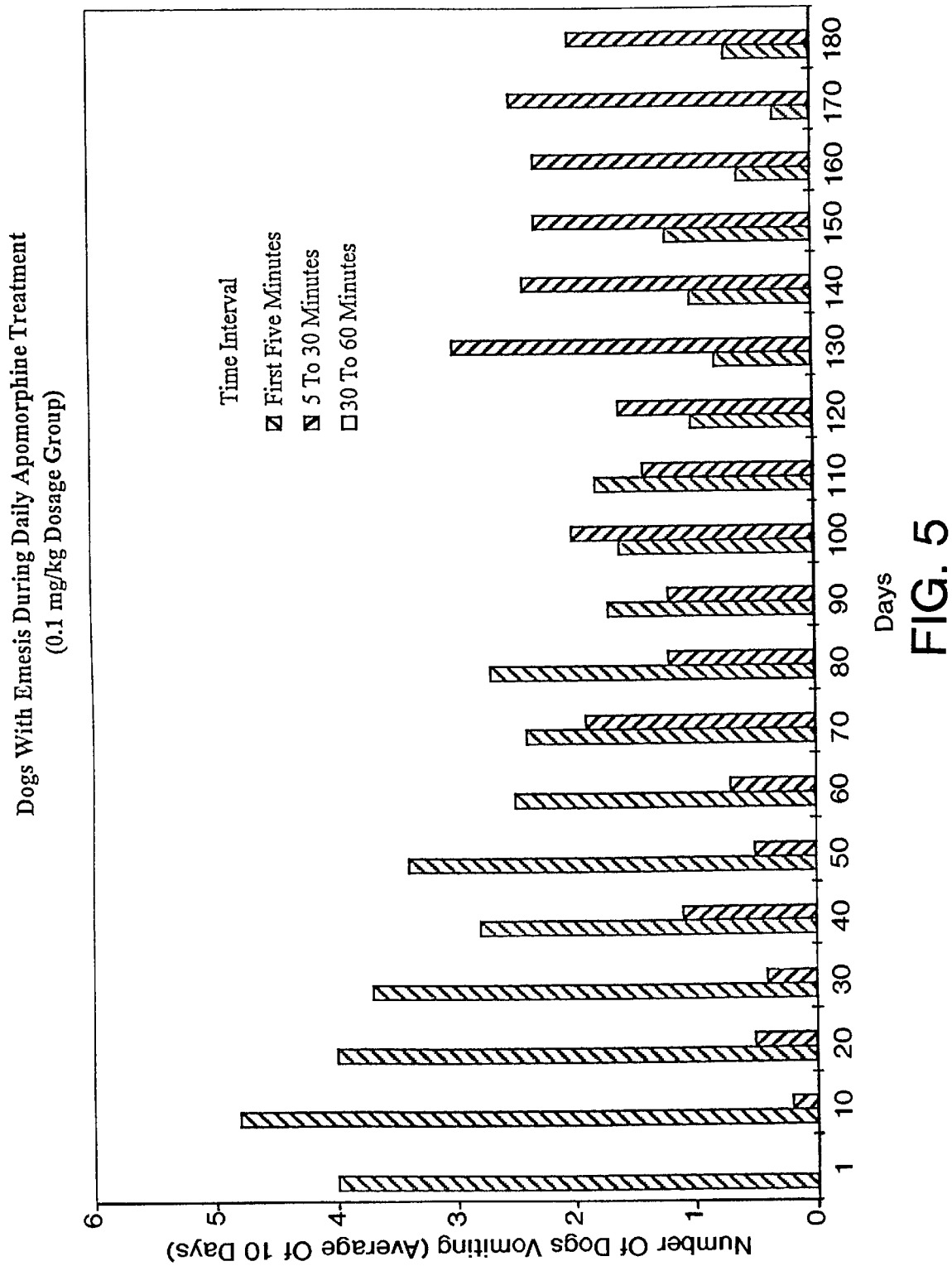
FIG. 5 is a plot over several days of number of dogs experiencing vomiting within three time periods following administration of 0.1 mg apomorphine per kg dog.
Figure 6:
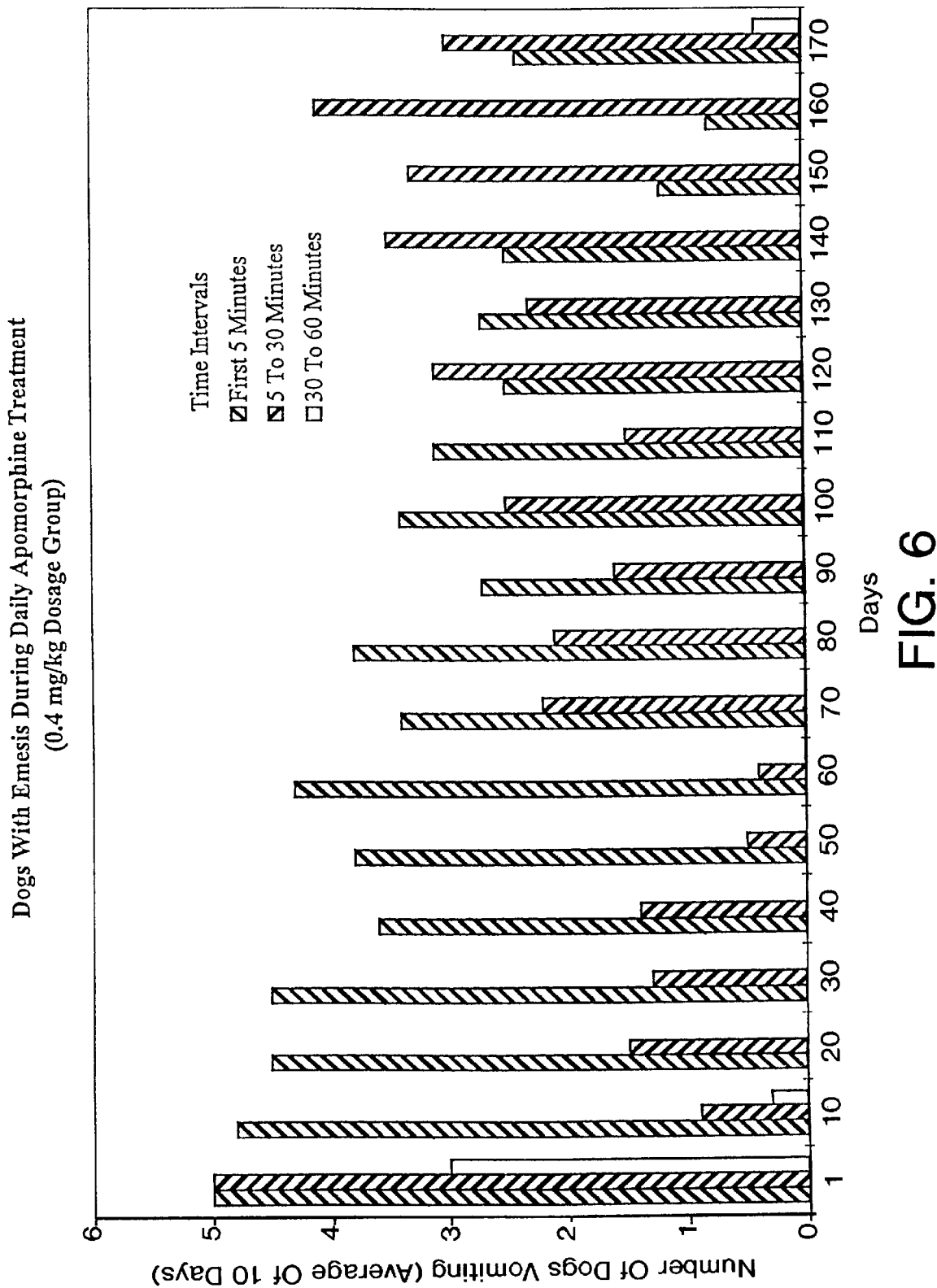
FIG. 6 is a plot over several days of number of dogs experiencing vomiting within three time periods following administration of 0.4 mg apomorphine per kg dog.

Vomiting and Retching in Dog Following Daily Subcutaneous Administration of Apomorphine HCl—Measurement of the Duration of Vomiting and Retching After Dosing In this dose defining study, subcutaneous apomorphine HCl was administered to dogs starting at 0.05 or 0.4 mg/kg. The dosages were eventually escalated. The duration of nausea/retching and vomiting were monitored and are reported in FIGS. 1 and 2. Dogs are known to be 5 to 10 times more sensitive than humans to apomorphine induced emesis.

At the lower doses, acclimatization of the animals as evidenced by the incidence of retching and vomiting occurred within 3 days of the initial dose. After 12 days the animals were challenged to a dose 100% greater than their acclimatized dose. Only a small increase in the duration of vomiting was noted which normalized by the end of the study. At the 0.4 mg/kg/day dose, acclimation was evident after about 10 days (see FIG. 2). Following 21 days of treatment at 0.4 mg/kg/day, the dose was escalated to 0.8 mg/kg/day with no evidence of an increase in vomiting/retching.

At day 28 the dose was escalated to 1.2 mg/kg/day. This dose produced a modest increase in the duration of vomiting and retching. However, this dose produced significant disturbances in locomotion and coordination due to the effect of the drug on the nigra-striatal movement center. The dose was reduced to 0.8 mg/kg/day where the movement disorders were again observed. This was believed to be the result of up-regulation of the dopamine receptor system in the higher brain, also observed in other species. Once the supersensitivity has been achieved in the CNS, a wash out period of about 4 to 6 weeks is required to establish homeostasis.

This study indicates that the treatment period with apomorphine HCl to produce a significant reduction in vomiting and retching is dose dependent. Generally, the average duration of the retching/vomiting period following the initial dose was about 30 minutes. This duration was reduced markedly to about 5 minutes following daily admistration. Further, once the acclimation had been established, increasing the dose by a 100% of the acclimation dose produced no corresponding increase in the duration of retching and vomiting.

EXAMPLE 2

Measurement of the Time to Maximum Number of Animals Acclimatized to the Side Effects of Daily Administration of Subcutaneous Apomorphine The number of animals retching or vomiting during selected time periods after subcutaneous administration of apomorphine HCl was recorded. Specifically, the occurrence of retching or vomiting was recorded for the following periods after apomorphine administration: 0 to 5 minutes, 5 to 30 minutes, and 30 to 60 minutes. This study provides a different view of data recorded in Example 1. The data studied in Example 1 revealed the average period of retching and vomiting, while in this Example the number of affected animals was examined in selected periods.

Observations were made at three different dosage levels, 0.04, 0.1 and 0.4 mg/kg/day. No dose escalation was attempted in this study. A group of five dogs was used for tests at each dosage level. The number of dogs in each dosage group with a retching or vomiting episode in each post-administration time period was recorded for daily administration over about 180 days. Ten day averages were calculated and plotted (see FIGS. 3 through 6).

At the higher, 0.4 dosage level, achieving a level of the 80 percent effective acclimation required daily treatment for about 3 months. The results as shown in FIGS. 3 through 6 indicate that individual variations do occur in a relatively refractory subject, and that acclimatization can be achieved by repeated treatment at an intolerated dose. The time to acclimatization is a function of the given dose, and the individual subject's predisposition to emesis.

Figure 7:
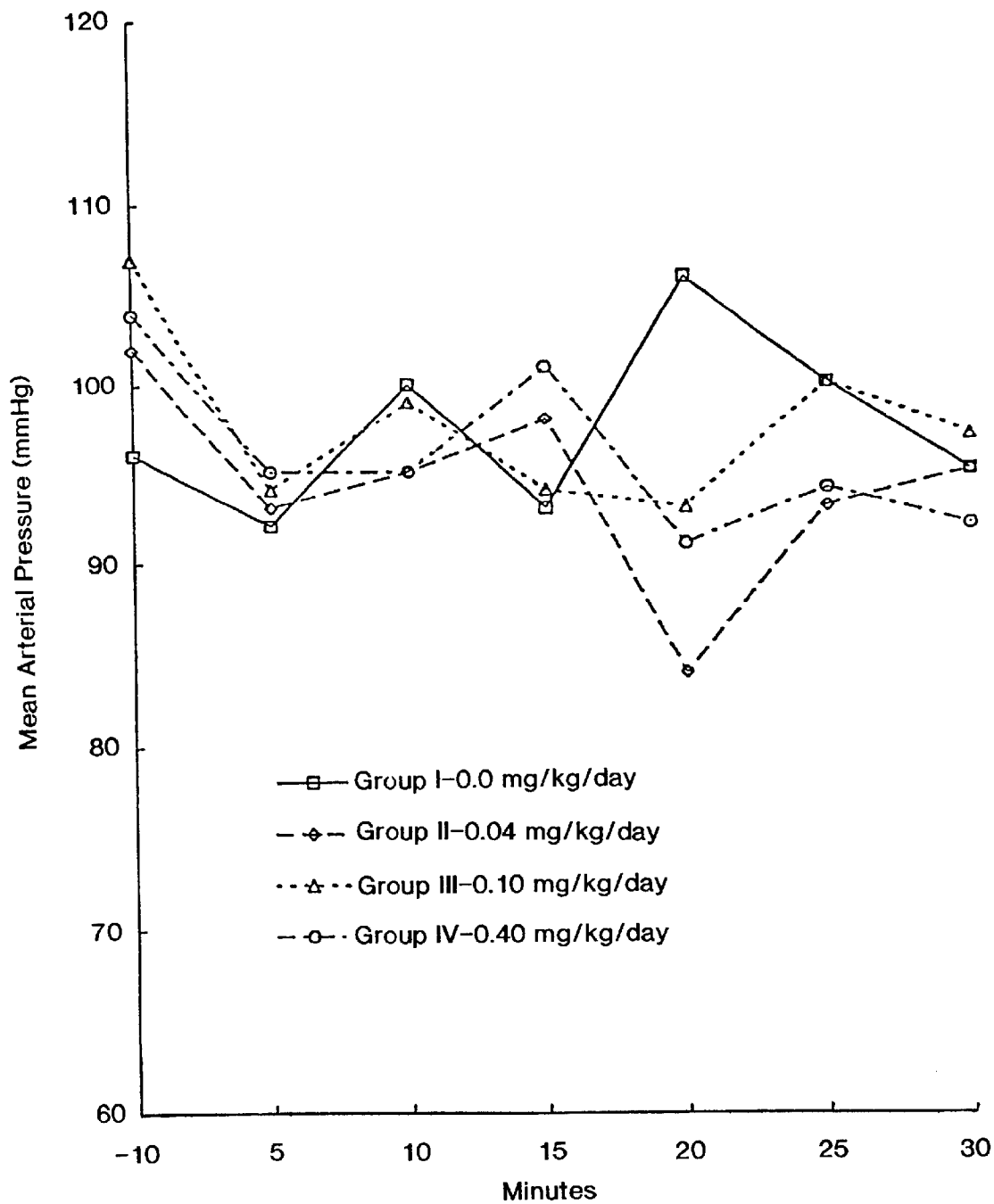
FIG. 7 is a plot of mean arterial pressure versus time for dogs receiving three different dosages of apomorphine measured after 5 months of daily apomorphine administration.
Figure 8:
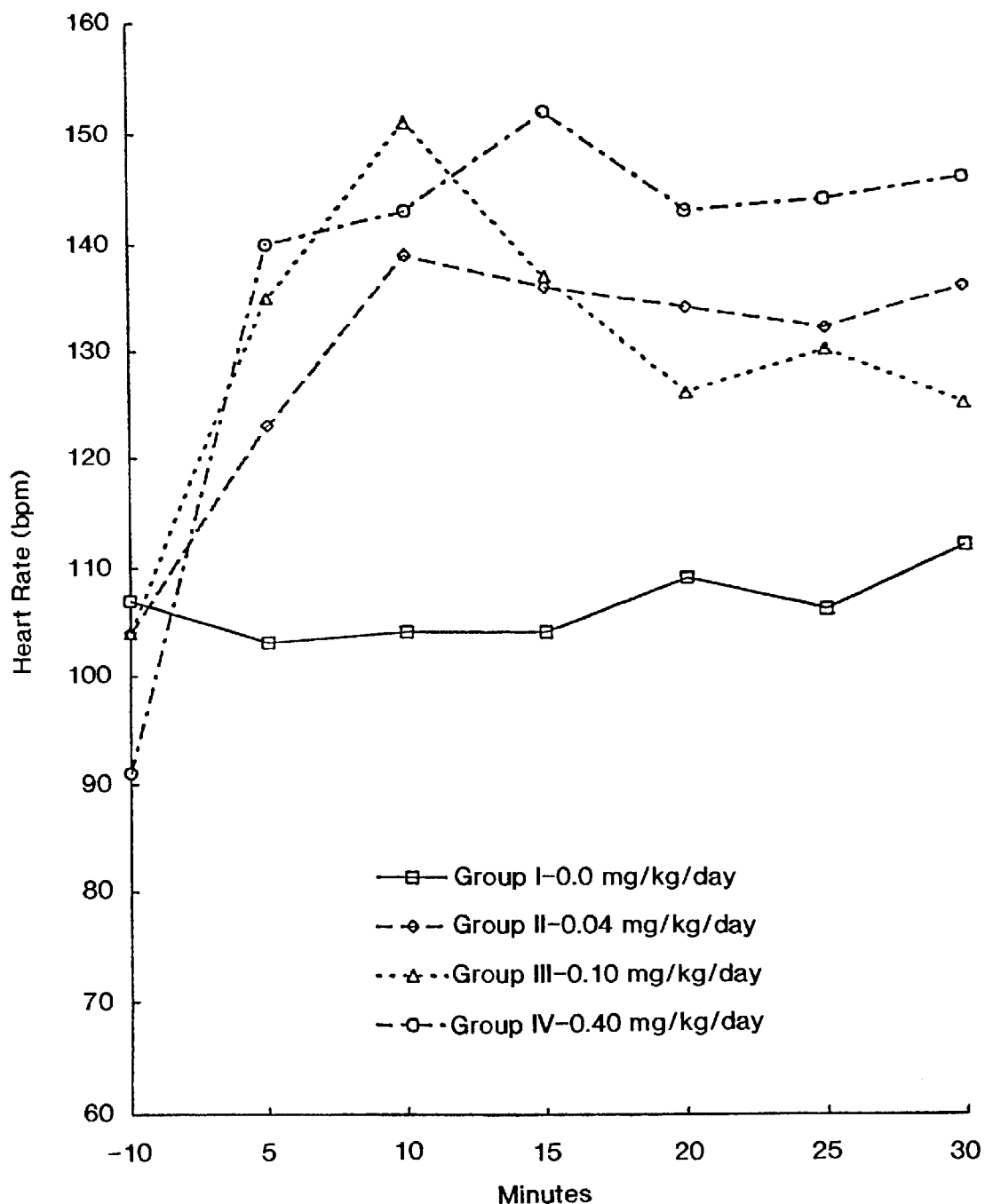
FIG. 8 is a plot of heart rate versus time for dogs receiving three different apomorphine dosages measured after 5 months of daily apomorphine administration.

Since many of the known side effects are the result of peripheral vasodilation, post-administration blood pressure and heart rates were measured for each dosage group following 5 months of chronic treatment (around day 150). The blood pressure and heart rates of an untreated group of dogs was evaluated for comparison purposes. The results are reported graphically in FIGS. 7 and 8. It was noted that tachycardia sometimes occurs following administration, though the net changes in blood pressure are not significantly different from the controls.

Following daily administration of apomorphine, peripheral vasodilation appears to be compensated by an increase in the cardiac output. Initially, badycardia was reported in some subjects exposed to apomorphine HCl. This effect is lost by acclimation of the vagus nerve dopamine receptor producing a compensated signal invoking an increase heart rate to account for the decreasing blood pressure.

Figure 9:
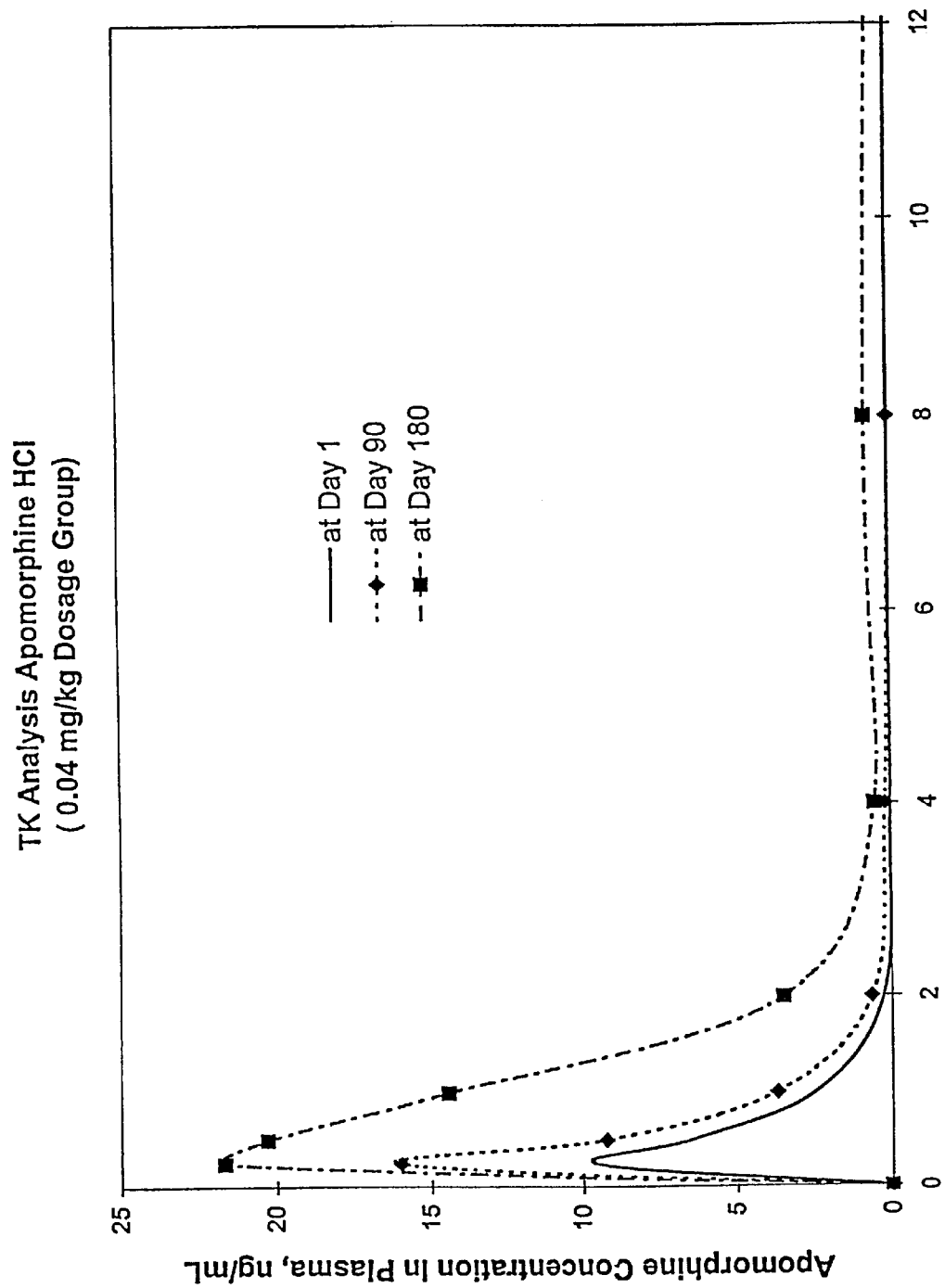
FIG. 9 is a plot of mean plasma concentrations of apomorphine versus time for dogs receiving 0.04 mg apomorphine per kilogram.
Figure 10:
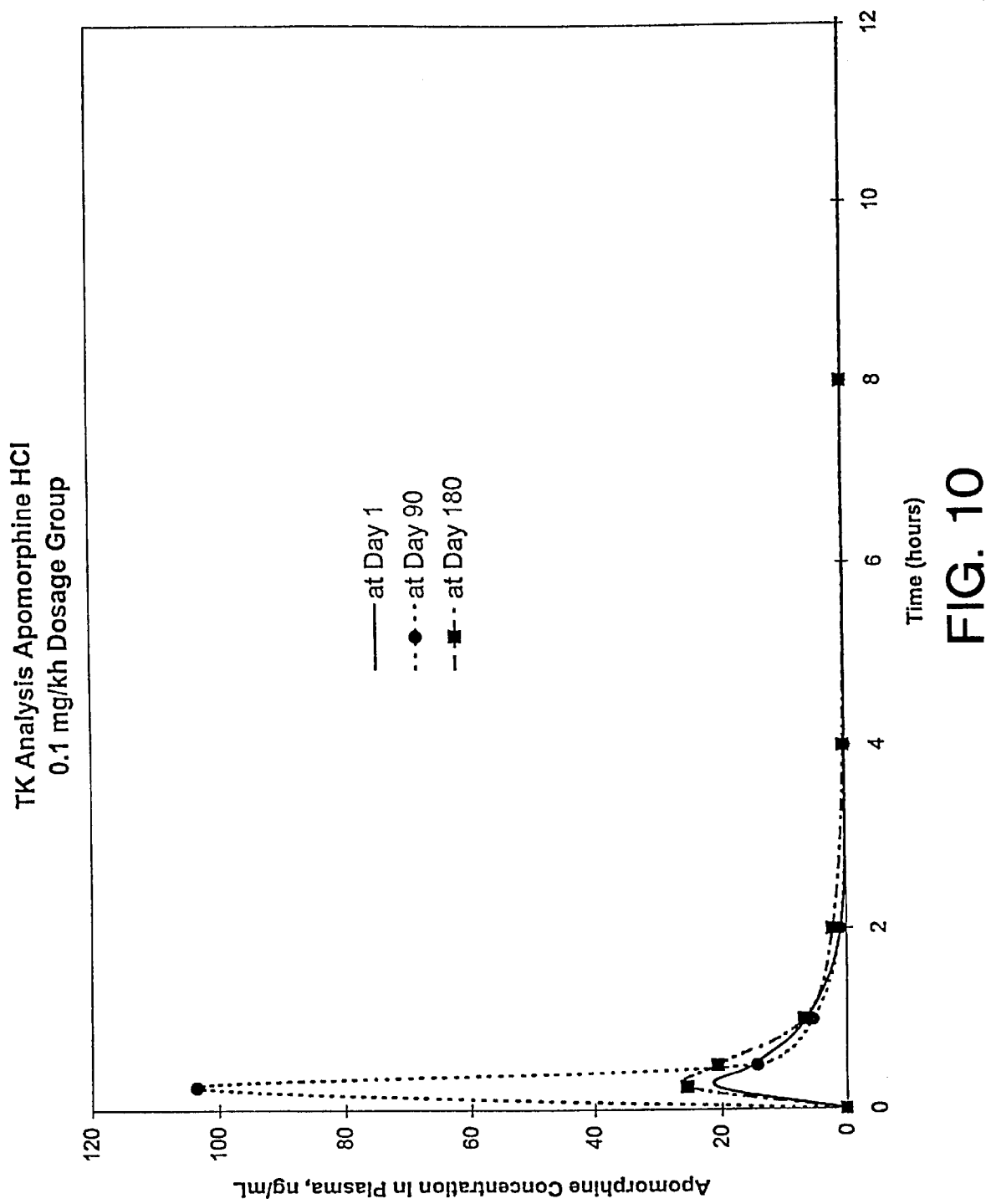
FIG. 10 is a plot of mean plasma concentrations of apomorphine versus time for dogs receiving 0.1 mg apomorphine per kilogram.
Figure 11:
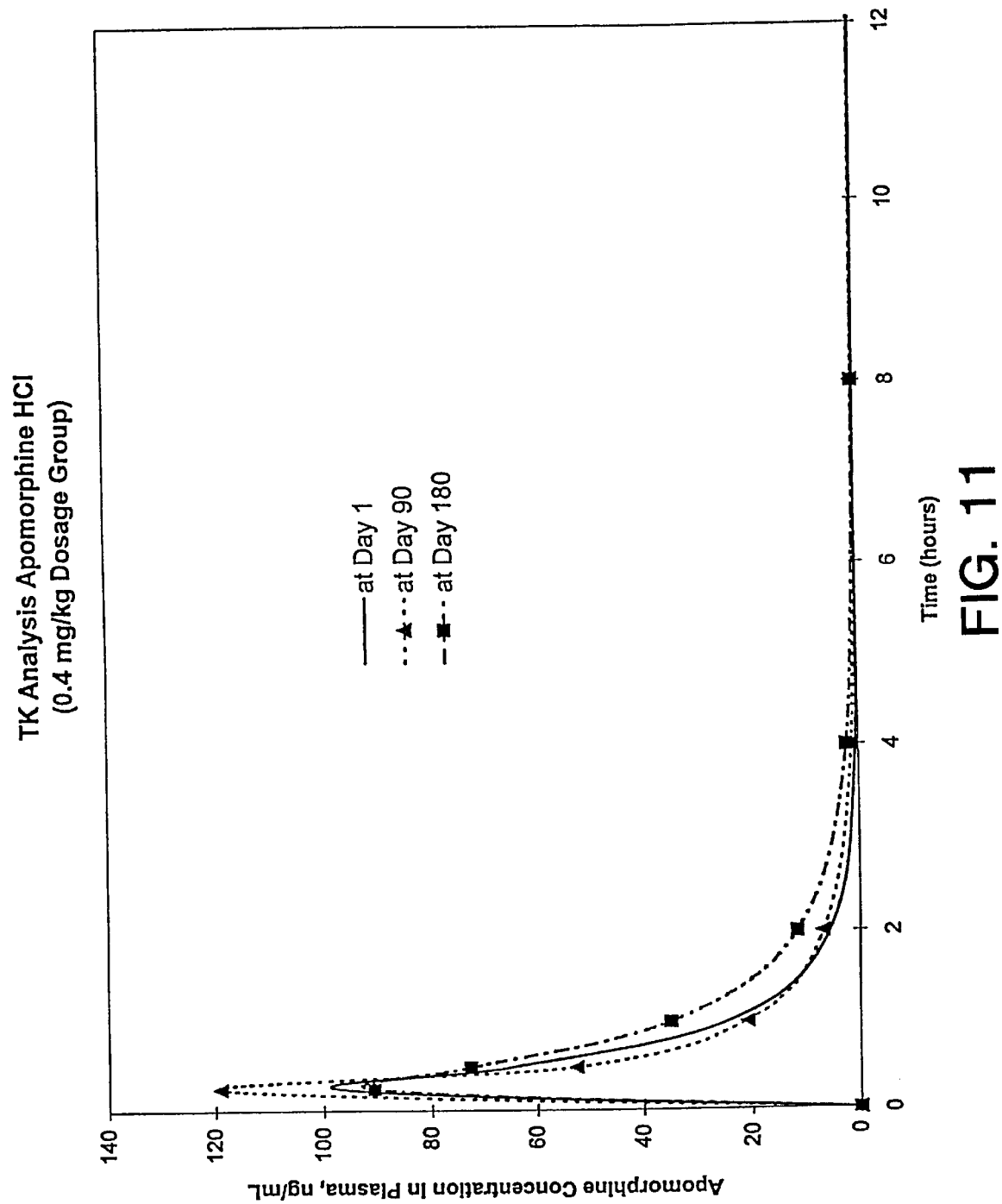
FIG. 11 is a plot of mean plasma concentrations of apomorphine versus time for dogs receiving 0.4 mg apomorphine per kilogram.

To assess whether the reduction in side effects could be attributable to changes in pharmacokinetic response, a plasma concentration profile study was conducted for each dosage group at day 1, day 90 and day 180. Specifically, plasma apomorphine concentration was measured at intervals over a period of 8 hours following administration. The results are reported in FIGS. 9 through 11.

No evidence of significant changes was noted in the area under curve (AUC), distribution, or elimination of the apomorphine among plasma concentration data for the day 1, day 90 or day 180 measurements. Therefore, the observed drop in side effects to apomorphine are not the result of significant changes in the pharmacokinetics.

EXAMPLE 3

Comparison of Sublingual, Oral and Subcutaneous Administration of Apomorphine HCl in Dog Dogs were exposed to a single dose of Apomorphine HCl, first by subcutaneous administration of 0.04 mg/kg, then subsequently at 3 day intervals to 0.2 mg/kg by sublingual and 0.2 mg/kg by oral routes. The quelling of the incidents of vomiting and/or retching is reported in Table II, below.

TABLE II

Duration Of Side Effects Following Subcutaneous,
Sublingual, And Oral Adminstration Of Apomorphine HCl In Dog[3]

| Time from Dose | Subcutaneous | Sublingual | Oral |
| --- | --- | --- | --- |
| 8 min. | 4 | 0 | 0 |
| 15 min. | 2 | 1 | 0 |
| 30 min. | 0 | 1 | 0 |
| Average Severity | 150.00% | 50.00% | 0.00% |

[3]Number of animals having nausea/vomiting at the posted time interval; 4 animals per group.

The foregoing results indicate that on initial treatment with a subcutaneous injection of apomorphine at about six times the sublingual bioavailable dose acclimatized the dogs to this subsequent dose. The pharmacokinetic analysis of the data is shown in Table III, below. The bioavailability of the drug was found to be about 13% via sublingual delivery. This value is consistent with previously reported findings in humans.

TABLE III

Bioavailability Of Apomorphine By
Route Of Adminstration In Dog

| | | Bioavailability |
| --- | --- | --- |
| Subcutaneous (0.04 mg/kg) | 483.56 ng/ml (min) | |
| Sublingual (0.2 mg/kg) | 327.1 ng/ml (min) | 13.53% |
| Oral (0.2 mg/kg) | 94.59 ng/ml (min) | 3.91% |

Human Studies

EXAMPLE 4

Pharmacokenetic Comparison of a 4-mg and 8-mg Sublingual Tablet to an Intravenous Injection of 1 mg of Apomorphine HCl This study compares the plasma concentration of apomorphine following two sublingual dosages of 4- or 8-mg tablets to a 1 mg intravenous bolus injection. The study was conducted in seven healthy male volunteers. The plasma was prepared and assayed using the method of Bianchi & Landi (J. Chromatography, 1985). The results are presented in Table IV, below.

TABLE IV

Pharmacokinetic Comparison

| | I.V. 1 mg | Apomorphine Tablet, 4 mg | Apomorphine Tablet, 8 mg |
| --- | --- | --- | --- |
| Route | i.v. | s.l. | s.l. |
| Number Of Subjects | 7 | 7 | 7 |
| Tablet(s) × Strength | — | 1 × 4 | 1 × 8 |
| Dose(mg/Kg) | 0.01 | 0.06 | 0.11 |
| $C_{max}$(ng/ml) | 8.3 | 0.83 | 2.07 |
| $T_{max}$(min) | 2.2 | 17.5 | 52.5 |
| AUC(ng/ml/min) | 207 | 31.6 | 283 |
| Cl(L/Hr/Kg) | 4.37 | — | — |
| Vd(L/Kg) | 3.35 | 2.33 | 2.07 |
| MRT(min) | 40.3 | 64.2 | 143.7 |
| T1/2(min) | 39.4 | 89.2 | 176.3 |
| F | — | 4.00% | 0.21 |

AUC = area under the curve
Cl = clearance
Vd = volume of distribution @ β stage.
Vd (SS) = volume of distribution steady state
MRT = mean residual time A drug plasma concentration of about 2.5 nanograms/milliliter is considered the threshold concentration ($C_{max}$) at which the onset of adverse effects, such as nausea, typically occur in human male subjects. When apomorphine is administered parenterally—as apomorphine hydrochloride—the threshold is readily surpassed. However, by sublingual administration of tablets, containing as much as 8 milligrams of apomorphine hydrochloride, the drug plasma concentration may be more readily maintained at approximately $C_{max}$.

EXAMPLE 5

Apomorphine HCl Sublingual Tablet Escalating Dose Tolerance Study for the Treatment of Psychogenic Male Erectile Dysfunction Example 5-Summary. This clinical study was conducted in three phases. In Phase 1 subjects were selected from among patients complaining of impotence by a thorough physiological and psychological assessment. For example, one step in the assessment process required candidates to undergo Rigiscan measurement of penile rigidity and circumference following administration of a placebo tablet in single blind fashion. Phase 2 consisted of a dose escalation (4, 6, and 8 mg tablets) administered on 4 visits. An out-patient phase was conducted as Phase 3. Patients were given apomorphine HCL tablets to use at home. Adverse events (side effects) attributable to the apomorphine HCL were reported in all three phases of the study.

Table IV, below, is a summary of the frequency of side effects to the number of patients in Escalation Phase (Phase 2) compared to Out-Patient Phase (Phase 3). During the dose escalation phase the frequency of side effects was noted to increase from 61.5% to 105.8% and began to decline for the 8-mg tablet to 94.2%. The frequency of side effects at the 4- and 6-mg doses were about one half and one third, respectively, compared to the patients initial exposure to these doses. The acclimatization evidence here demonstrates the utility of dose escalation for reduction of overall side effects. Side effects reported in this study were: Nausea, Fatigue, Dizziness, Sweating, Yawning, Hypotension and Vomiting.

TABLE IV

Human Study Summary
Incidence Of Side Effects Reported During
Dose Escalation And Out-Patient Treatment With
Apomorphine HCl Sublingual Tablet

| | Phase 2 | | | Phase 3 | | |
| --- | --- | --- | --- | --- | --- | --- |
| Dose (mg/week) | 4 | 6 | 8 | 4 | 6 | 8 |
| Total Number of Adverse Events | 31 | 58 | 50 | 15 | 13 | 8 |

Table IV demonstrates that an escalating weekly exposure to apomorphine will be followed initially by an increase in the side effects until acclimation is achieved. The number and severity of the side effects reported by subjects subsequently decreased.

Example-5 Detailed Description (Clinical Study #94-03-01). The human study was conducted in three separate phases. Phase 1 consisted of selecting appropriate subjects and obtaining baseline information on sexual performance for each subject. Phase 2 consisted of dose escalation where subjects were administered increasing doses of apomorphine during a four-week period. Finally, phase 3 consisted of a five-week take-home trial where patients administered to themselves constant doses of apomorphine prior to sexual intercourse.

Phase 1: Subject Selection

Participating patients were selected from among those that initially presented with the complaint of impotence. These patients underwent a thorough urological assessment by a urologist as well as an assessment by a psychiatrist (See "Baseline" column in Table VII, below).

Diagnostic testing for erectile difficulties was extensive and included the following: biochemical profile, nocturnal penile tumescence (NPT) monitoring, Doppler flow studies, biothesiometry, corporal calibration testing with an intracorporal injection of triple therapy and dynamic cavernosometry. These tests were used to rule out any arterial, venous or peripheral neural causality of impotence. Any patients with abnormalities in any of these three areas were excluded from entry to the trials.

Subjects were also excluded for any evidence of erectile dysfunction due to other non-psychogenic causes (e.g., relational discord), any personal history of endocrine disease (e.g., diabetes mellitus, multiple sclerosis, cancer, cardiac disease, drug or alcohol abuse within the past twelve months, any history of hypogonadism or hyperprolactinemia, use of penile prosthesis, and several other conditions. Table VI below, is a non-exhaustive list of inclusion/exclusion criteria for the present study.

TABLE VI

Inclusion/Exclusion Criteria

A. INCLUSION CRITERIA:

1. Signed, written informed consent has been obtained;
2. Subject is heterosexual male between 18 and 65 years of age;
3. Diagnosis of psychogenic impotence as evidenced by documentation of:
   a. Unsuccessful intercourse with partner for at least six months prior to entry; and
   b. Documented report of ability to attain or maintain an erection of sufficient quality and duration for intercourse during the 3 months prior to entry as evidenced by morning erections, masturbation, and/or sexual foreplay;
4. Subject is presently in a stable, heterosexual relationship;
5. Subject and partner agree to at least one attempt at vaginal intercourse each week during the study;
6. Subject and partner agree to maintain effective birth control to prevent pregnancy during the study;
7. Subject is in good general health; and
8. Subject is willing to comply with study procedures.

B. EXCLUSION CRITERIA:

1. Subject is without evidence of male erectile dysfunction due to non-psychogenic causes such as relational discord, physiologic or organic dysfunction;
2. Prior concomitant use of any of the following medications or treatments within the restricted time period as follows:

TABLE VI-continued

Inclusion/Exclusion Criteria

| Medication/Treatment | Washout prior to entry and throughout study |
|---|---|
| Diuretics (hydrochlorothiazide, furosemide, amiloride, etc.) | 30 days |
| Calcium Channel Blockers (verapamil, nifedipine, etc.) | 30 days |
| Other antihypertensive agents (captopril, methyldopa, etc.) | 30 days |
| Other investigational drugs | 30 days |
| Anti-anxiety/sedative agents (Elavil, Valium, etc.) | 30 days |
| Tricyclic antidepressants, MAO inhibitors, and other mood elevating agents (Prozac, anitryptilline, Nardil, Parnate) | 60 days |
| Antipsychotic agents (clozapine, chlorpromazine, etc.) | 90 days |
| Vasodilators (hydralazine, diazoxide, etc.) | 90 days |
| Sympathomimetic agents (epinephrine, dopamine, etc.) | 90 days |
| Parasympathetic agents (methacholine, bethanecol, etc.) | 90 days |
| Beta blockers (atenolol, propranolol, etc.) | 90 days |
| Sex hormone therapy (testosterone) | 90 days |
| Chemotherapeutic agents (methachlorethamine, BCNU, methotrexate, etc.) | 2 years |

3. Presence of any disease related to non-psychogenic impotence including but not limited to the following conditions:
   a. Endocrine disease (diabetes mellitus, Addison's disease, etc.);
   b. Multiple sclerosis;
   c. Neurologic disease or injury (spinal cord injury or lesion, neuropathy, etc.);
   d. Vascular disease (Leriche Syndrome, aneurysm, atherosclerosis, cerebrovascular disease, etc.);
   e. Cancer;
   f. Renal disease;
   g. Hepatic disease;
   h. Cardiac disease (including hypotension, angina, history of MI, angioplasty, CABG, arrhythmia, etc.);
   i. Pelvic disease, trauma, or injury; and
   j. Psychiatric disorders other than psychogenic impotence (including antisocial disorders, depression, schizophrenia, etc.);
4. History of hypogonadism or hyperprolactinernia (serum prolactin > 30 ng/ml + SI conversion);
5. Documented history of serum testosterone level <300 or >1000 ng/dL + SI conversion (or above or below the normal range for the laboratory) within 3 months prior to entry;
6. Use of penile prosthesis at any time in the past;
7. Presence of postural hypotension evidenced by resting blood pressure <90/50 mmHg in sitting position or hypertension evidenced by resting blood pressure >170/110 mmHg;
8. History of drug or alcohol abuse within past year;
9. Subject not willing to comply with study procedures.

Male patients who met all criteria were diagnosed as having impotence primarily of a psychogenic origin. If there were no known medical contraindications to the use of a dopaminergic medication they were offered entry into an APO trial.

TABLE VII

Study Parameter Schedule

| PARAMETER | Baseline (−1) Week* | Treatment 1 Visit 1 Day 1 | Treatment 2 Visit 2 Day 8 | Treatment 3 Visit 3 Day 15 | Treatment 4 Visit 4 Day 22 | Treatment 5 Visit 5 Day 29 | Treatment 6 Home Use 35 ± 5 days | Termination Visit Visit 7 |
|---|---|---|---|---|---|---|---|---|
| Inclusion/Exclusion | X | | | | | | | |
| Medical History | X | | | | | | | |
| Psychosexual History | X | | | | | | | |
| Physical Exam | X | | | | | | | X |
| Vital Signs | X | X | X | X | X | X | | X |

TABLE VII-continued

Study Parameter Schedule

| PARAMETER | Baseline (−1) Week* | Treatment 1 Visit 1 Day 1 | Treatment 2 Visit 2 Day 8 | Treatment 3 Visit 3 Day 15 | Treatment 4 Visit 4 Day 22 | Treatment 5 Visit 5 Day 29 | Treatment 6 Home Use 35 ± 5 days | Termination Visit Visit 7 |
|---|---|---|---|---|---|---|---|---|
| Vital Signs Post | | X | X | X | X | X | | |
| ECG | X | | | | | | | |
| Concomitant Medications | X | X | X | X | X | X | X | X |
| Hematology | X | | | | | X | | X |
| Blood Chemistry | X | | | | | X | | X |
| Prolactin Level | X | | | | | | | |
| Testosterone Level | X | | | | | | | |
| Urinalysis | X | | | | X | X | | X |
| Placebo Administration | | X | | | | | | |
| Study Drug | | | X | X | X | X | X | |
| Penile Measurements | | X | X | X | X | X | | |
| Subject Questionnaire | X | X | X | X | X | X | X | X |
| Wife/Partner | X | | | | | | X | X |
| Adverse Effects | | X | X | X | X | X | X | X |

*Seven days before treatment period

Fifty males diagnosed as having psychogenic male erectile dysfunction (MED) were enrolled into the three phase trial from four different testing sites, as shown by Table VII below.

TABLE VIII

Subject Accountability

| Site No. | No. of Subjects Enrolled | No. of Subjects Completed All Phases | No. of Subjects Prematurely Terminated |
|---|---|---|---|
| #1 Kingston General Hospital | 11 | 9 | 2 |
| #2 Royal Victoria Hospital | 16 | 12 | 4 |
| #3 Columbia Presbyterian Medical Center | 14 | 11 | 3 |
| #4 University of California at San Francisco | 9 | 7 | 2 |
| total | 50 | 39 | 11 |

The investigations were conducted by Dr. Jeremy Heaton, M.D., at Site #1 (Kingston General Hospital, Kingston, ON, Canada); Dr. Magdy M. Hassouna, M.D., at Site #2 (Royal Victoria Hospital, Montreal, PQ, Canada); Dr. Ridwan Shabsigh, M.D., at Site #3 (Columbia Presbyterian Medical Center, New York, N.Y.); and Dr. Emil Tanagho, M.D., at Site #4 (University of California at San Francisco, San Francisco, Calif.).

Each of the selected subjects' penile erectile response (measured with the RIGISCAN™ ambulatory tumescence monitor) was evaluated using the scoring system as set out in Table IX, below.

TABLE IX

RIGISCAN™ Scoring

| 1. Maximum increase in penile circumference | | 2. Maximum penile rigidity | |
|---|---|---|---|
| Circumference (cms.) | Score | Rigidity (%) | Score |
| 0.0–<0.5 | 0 | 0–<10 | 0 |
| 0.5–<1.0 | 1 | 10–<20 | 1 |
| 1.0–<1.5 | 2 | 20–<30 | 2 |
| 1.5–<2.0 | 3 | 30–<40 | 3 |
| 2.0–<2.5 lasts <1 min. | 4 | 40–<50 | 4 |
| 2.5 or more lasts <1 min. | 5 | 50–<60 | 5 |
| 2.0–<2.5 lasts ≧1 min. | 6 | 60–<70 | 6 |
| | | 70–<80 | 7 |
| 2.5 or more lasts ≧1 min. | 7 | 80–<90 | 8 |
| 3.0 or more lasts ≧5 min. | 8 | 90–100 | 9 |
| 3.0 or more lasts ≧10 min. | 9 | | |
| Maximum increase in: | Score: | Maximum: | Score: |
| A. penile tip circumference: | — | A. penile tip rigidity | — |
| B. penile basal circumference: | — | B. penile basal rigidity | — |

The combining of the scores of A, B, C, and D from Table IX yields a total score for each subject. A total score of less than 16 for any individual subject indicates erectile dysfunction.

To complete this phase, each of the subjects were given a placebo tablet for sublingual administration and then viewed a thirty minute video consisting of two ten-minute erotic sequences separated by a ten-minute neutral sequence. The subjects then completed a visual analog scale (VAS) questionnaire, such as the one shown in FIG. 17, about their feelings and well-being.

After marking each of the thirteen data categories by placing a small vertical line at some point on the horizontal line between the two opposing conditions, a score was given based upon the distance of the mark from the left end of the horizontal line. The scores were marked in the box to the right of each category and later used for statistical analysis.

The VAS data compiled on the fifty subjects was used in the study for baseline information, as shown in Tables Xa–c, below. Table Xa gives the mean, SEM, median and range scores for several demographic categories for all sites combined, as well as each individual site as listed in Table VII, above. Table Xb shows the mean, SEM, median and range scores for all sites combined, and each individual site regarding the subjects' satisfaction with his recent and overall sexual performance and erection. Table Xc shows the mean, SEM, median and range scores for all sites combined, and each individual site regarding the subjects' erection results and frequency of sexual intercourse.

TABLE Xa

Baseline Information On Sexual Performance
All Patients

|  | All Sites Combined | Site 1 | Site 2 | Site 3 | Site 4 |
|---|---|---|---|---|---|
| Number of Patients | 50 | 11 | 16 | 14 | 9 |
| Age (years) | | | | | |
| Mean | 48.7 | 49.4 | 49.8 | 49.4 | 45.1 |
| SEM | 1.433 | 3.540 | 2.446 | 2.655 | 3.310 |
| Median | 50.5 | 46.0 | 53.5 | 51.5 | 46.0 |
| Range | 26–69 | 33–69 | 33–62 | 26–62 | 30–60 |
| N | 50 | 11 | 16 | 14 | 9 |
| Race | | | | | |
| Asian | 1 (2.0%) | 0 (0.0%) | 0 (0.0%) | 0 (0.0%) | 1 (11.1%) |
| Black | 6 (12.0%) | 0 (0.0%) | 2 (12.5%) | 3 (21.4%) | 1 (11.1%) |
| Hispanic | 3 (6.0%) | 0 (0.0%) | 0 (0.0%) | 3 (21.4%) | 0 (0.0%) |
| White | 40 (80.0%) | 11 (100.0%) | 14 (87.5%) | 8 (57.1%) | 7 (77.8%) |
| Height (cm) | | | | | |
| Mean | 175.4 | 175.1 | 169.3 | 178.8 | 181.5 |
| SEM | 1.123 | 1.331 | 1.690 | 2.150 | 1.934 |
| Median | 175.0 | 175.0 | 171.3 | 179.7 | 180.3 |
| Range | 149.5–196 | 168–180 | 149.5–176 | 165.1–196 | 174.8–193 |
| N | 50 | 11 | 16 | 14 | 9 |
| Weight (kg) | | | | | |
| Mean | 81.7 | 81.3 | 78.3 | 87.5 | 79.2 |
| SEM | 1.691 | 2.666 | 2.797 | 3.677 | 4.032 |
| Median | 80.0 | 83.9 | 75.0 | 85.9 | 80.4 |
| Range | 60–111.2 | 68–96 | 65.8–104.5 | 63.6–111.2 | 60–97.6 |
| N | 50 | 11 | 16 | 14 | 9 |

TABLE Xb

Baseline Information On Sexual Performance
All Patients

|  | All Sites Combined | Site 1 | Site 2 | Site 3 | Site 4 |
|---|---|---|---|---|---|
| Overall Satisfaction Level With Sexual Performance Within Past Two Months [1] | | | | | |
| Mean | 17.7 | 16.3 | 16.3 | 24.6 | 10.9 |
| SEM | 2.491 | 4.249 | 3.398 | 6.342 | 4.880 |
| Median | 14.0 | 16.0 | 16.0 | 12.0 | 4.0 |
| Range | 0–62 | 1–46 | 0–51 | 0–62 | 0–39 |
| N | 49 | 11 | 15 | 14 | 9 |
| Level of Satisfaction With Most Recent Attempt at Intercourse [1] | | | | | |
| Mean | 22.5 | 17.3 | 21.0 | 32.2 | 16.1 |
| SEM | 3.720 | 6.716 | 7.223 | 8.113 | 6.033 |
| Median | 9.0 | 5.0 | 7.0 | 21.0 | 8.0 |
| Range | 0–100 | 0–69 | 0–87 | 0–100 | 0–52 |
| N | 49 | 11 | 15 | 14 | 9 |
| Results of Erection During Most Recent Attempt at intercourse [2] | | | | | |
| Mean | 35.3 | 32.9 | 25.3 | 49.0 | 50.0 |
| SEM | 4.653 | 8.857 | 8.143 | 8.152 | 12.119 |
| Median | 30.0 | 22.0 | 12.0 | 41.0 | 50.0 |
| Range | 0–100 | 1–80 | 1–96 | 7–100 | 0–100 |

TABLE Xb-continued

Baseline Information On Sexual Performance
All Patients

|   | All Sites Combined | Site 1 | Site 2 | Site 3 | Site 4 |
|---|---|---|---|---|---|
| N | 49 | 11 | 15 | 14 | 9 |

[1] Visual Analog Scale: 0 = Extremely Unsatisfied, 100 = Extremely Satisfied
[2] Visual Analog Scale: 0 = No Erection, 100 = Rigid Erection Suitable for Penetration

TABLE Xc

Baseline Information On Sexual Performance
All Patients

|   | All Sites Combined | Site 1 | Site 2 | Site 3 | Site 4 |
|---|---|---|---|---|---|
| Overall Erection Results When Attempting Intercourse [2] | | | | | |
| Mean | 41.1 | 32.3 | 42.1 | 41.9 | 48.9 |
| SEM | 4.093 | 5.955 | 5.536 | 7.642 | 9.866 |
| Median | 40.0 | 29.0 | 21.0 | 38.0 | 49.0 |
| Range | 0–100 | 0–54 | 3–100 | 4–100 | 1–96 |
| N | 49 | 11 | 15 | 14 | 9 |
| Successfully Complete Intercourse During Most Recent Attempt? | | | | | |
| (No Response) | 1 (2.0%) | 0 (0.0%) | 1 (6.3%) | 0 (0.0%) | 0 (0.0%) |
| NO | 35 (70.0%) | 10 (90.9%) | 13 (81.3%) | 6 (42.9%) | 6 (66.7%) |
| YES | 14 (2S.0%) | 1 (9.1%) | 2 (12.5%) | 8 (57.1%) | 3 (33.3%) |
| Frequency of Attempts at Sexual Intercourse | | | | | |
| RARELY OR NEVER | 3 (6.0%) | 0 (0.0%) | 0 (0.0%) | 0 (0.0%) | 3 (33.3%) |
| 2–6 TIMES A YEAR | 4 (8.0%) | 0 (0.0%) | 1 (6.3%) | 2 (14.3%) | 1 (11.1%) |
| ONCE A MONTH | 5 (10.0%) | 1 (9.1 %) | 0 (0.0%) | 2 (14.3%) | 2 (22.2%) |
| 2–3 TIMES A MONTH | 16 (32.0%) | 5 (45.5%) | 5 (31.3%) | 3 (21.4%) | 3 (33.3%) |
| 4–5 TIMES A MONTH | 10 (20.0%) | 2 (15.2%) | 7 (43.5%) | 1 (7.1%) | 0 (0.0%) |
| 6–7 TIMES A MONTH | 7 (14.0%) | 3 (27.3%) | 2 (12.5%) | 2 (14.3%) | 0 (0.0%) |
| 8 TIMES OR MORE A MONTH | 5 (10.0%) | 0 (0.0%) | 1 (6.3%) | 4 (25.6%) | 0 (0.0%) |

[2] Visual Analog Scale: 0 = No Erection, 100 = Rigid Erection Suitable for Penetration Phase II: Escalating dose Instructions were given regarding the protocol by the research clinician, and an informed consent was obtained. Patients were advised that they were free to withdraw from the trial at any time without penalty or prejudice. They were tested on four separate days at four separate doses (placebo and three active medication doses) with an interval of no less than six days between visits (i.e., one visit per week).

In this phase, patients were seated in a comfortable chair and a RIGISCAN™ ambulatory tumescence monitor (Dacomed Corp., Minneapolis, Minn.) was connected to the patient and the computer was set in the real time monitoring mode. Blood pressure and heart rate were recorded pre-dosing with APO or placebo and at the end of the testing session. Visual analogue scales (VAS) were completed by the patient pre-dosing as well as post-dosing (at the end of the testing session). These scales, as in phase I, reflected the patient's sense of well being, level of sedation, tranquilization, anxiousness, arousal and any changes in yawning behavior.

In a single-blind fashion, an apomorphine hydrochloride tablet (4, 6, or 8 mg) or placebo was administered to the patient sublingually during each of the four visits. Because of the possibility of nausea and the tolerance to this effect that prior dosing conveys, the patient was given increasing doses of the apomorphine at each testing, with the placebo being randomly assigned at one of the visits. Patients were instructed not to swallow the medication, but to keep it under their tongue and allow it to be absorbed there.

Symptoms as they were volunteered were recorded by the research clinician. If the patient complained of nausea or felt unwell in any way he was asked if he wanted to abort the trial. If the trial was aborted, the patient was given the choice of having Gravol 50 mg p.o. (an anti-emetic) administered at that time or enduring the adverse events as they arose. In either event, the patient was monitored by the research clinician until all side-effects had subsided. The patient was asked to return the following week for the next scheduled dose.

Patients not experiencing nausea or any other significant adverse effects within fifteen minutes post-dosing with APO or placebo viewed segments of standardized erotic videos to provide sexual stimulation. The following sequence of videos was viewed: a ten minute erotic video (Erotic #1), a neutral video (Neutral) lasting between five and ten minutes in duration and finally another ten minute erotic video (Erotic #2). The duration of the testing session for each dose level lasted between 45 and 60 minutes. After determining the most effective dose of apomorphine for the patient, he was then offered APO tablets at that dose for the final phase of the study.

Phase III: take-home

During the five-week, home-use phase, subjects were to attempt coitus at least once each week after taking a single APO tablet. After each attempt, the subject and his partner completed a Sexual Function questionnaire (See FIGS. 15 and 16) which was later evaluated and used for final statistical analysis. Subjects had a final evaluation at the end of this phase.

The Results

Figure 12:
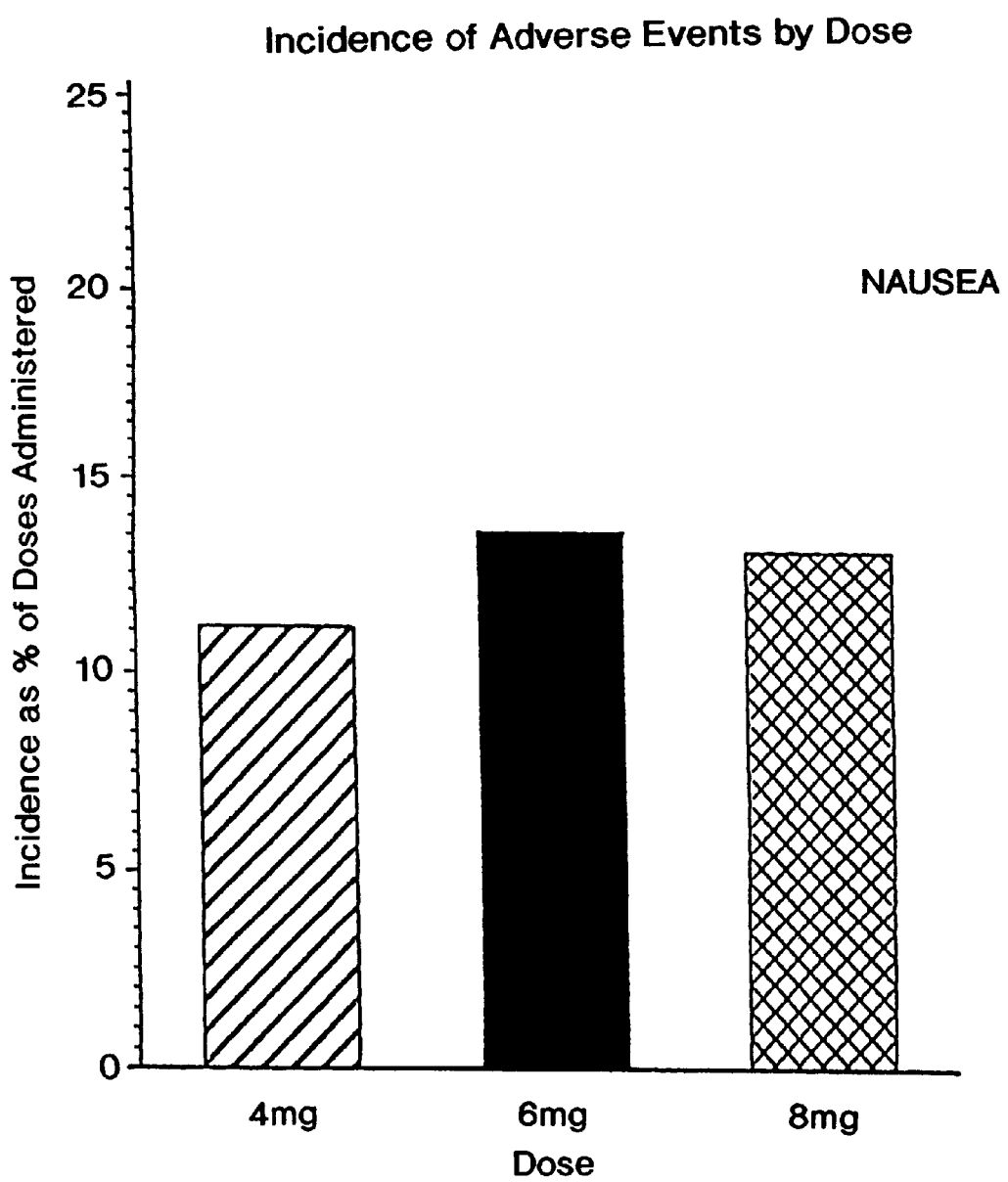
FIG. 12 is a bar graph which represents the incidence of nausea (an adverse event) in humans at each dosage administered as a percentage of the doses administered.

One aim of this study was to determine the safety and tolerance of APO in the treatment of MED. Several adverse events directly linked with administration of APO in humans were expected: yawning, nausea, vomiting, and cardiovascular effects. Indeed, nausea was the primary adverse event reported in this trial (46% of the subject receiving 6 mg. APO reported nausea), but the overall incidence for all administered doses was less than 13% of the subjects and only two cases were considered severe. FIG. 12 is a bar graph which shows the incidence of nausea as a percentage of doses administered for each level.

Figure 13:
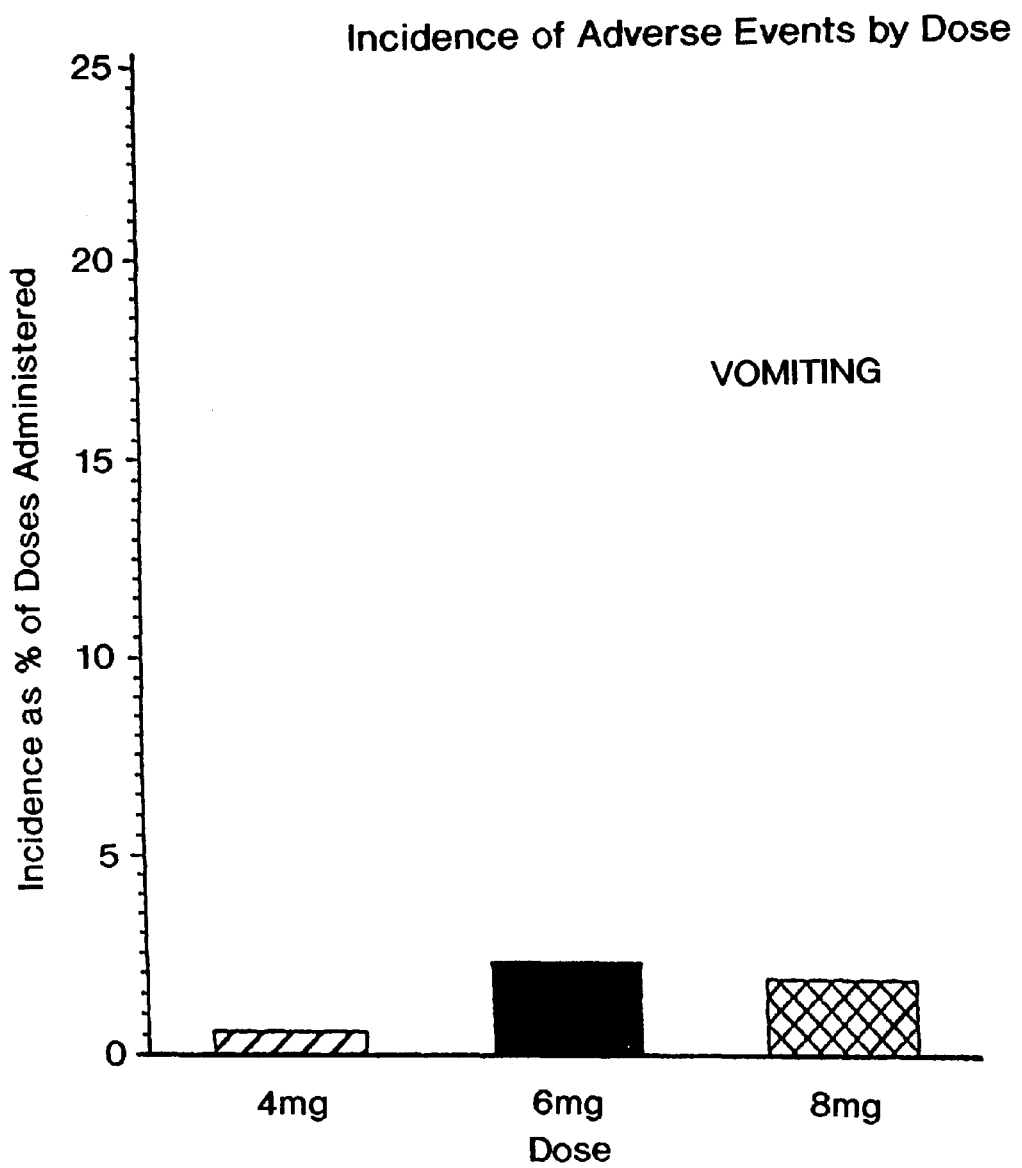
FIG. 13 is a bar graph which represents the incidence of vomiting (an adverse event) in humans at each dosage administered as a percentage of the doses administered.

The incidence of vomiting, as illustrated in FIG. 13, was less than 3% for each administered dose. The greatest incidence of vomiting, approximately 2.5%, was also at the 6 mg dose.

Hypotension was reported as an adverse event in some subjects in this study, along with bradycardia, dizziness, syncope, and pallor. Only single cases of hypotension and pallor were judged severe in this study. Increased sweating and fatigue were also reported. One of the cases of increased sweating was considered severe. The other severe adverse events (mouth edema, dysphagia, upper respiratory tract infection) were judged unrelated to treatment.

Changes in the serum chemistry values and vital signs paralleled the adverse event reports. There were no clinically significant changes except for one subject judged to have abnormal liver function of unknown origin. There were no clinically significant changes in the blood or urinalysis values due to drug. While fifty (50) patients were enrolled in the study, only thirty-nine (39) patients completed all phases of the study and were considered valuable. An additional four patients completed the drug treatment but were considered not valuable because of incomplete information or failing to return case report forms. In all, twenty-three (23) patients had reported specific adverse effects, called adverse events herein, associated with apomorphine in one or more phases of the study.

The data was analyzed by an inspection of the reported adverse events, the given dose of apomorphine and the phase of the study, i.e., in-patient (dose escalating) or take-home (constant dose) phases. A brief data summary of the adverse events reported by each of the twenty-three patients, as shown in Table XI, below, clearly demonstrates the effects of dose escalation on the reduction in the reported numbers of adverse events (A.E.'s) in the constant dose phase.

TABLE XI

Analysis of Drug Related Adverse Events

| Patient No. | In-Patient A.E.'s | at dose(s) | Take-Home A.E.'s | at dose(s) | Anti-Emetic In Patient | Take Home |
|---|---|---|---|---|---|---|
| 1002 | 6 | 6 & 8 | 0 | 4 | 1 | 0 |
| 1003 | 6 | 6 & 8 | 1 | 6 | 1 | 0 |
| 1004 | 10 | 4, 6, & 8 | 0 | 6 | 0 | 0 |
| 1005 | 1 | 8 | 0 | 8 | 0 | 0 |
| 1007 | 22 | 4, 6, & 8 | 0 | 6 | 1 | 0 |
| 1010 | 11 | 4, 6, & 8 | 0 | 6 | 1 | 0 |
| 1011 | 1 | 6 | 0 | 4 | 0 | 0 |
| 2001 | 2 | 8 | 0 | 4 | 0 | 0 |
| 2002 | 4 | 6 & 8 | 0 | 4 | 1 | 0 |
| 2005 | 2 | 8 | 6 | 8 | 0 | 1 |
| 2010 | 2 | 6 & 8 | 0 | 4 | 0 | 0 |
| 2012 | 3 | 4 | 0 | 4 | 0 | 0 |
| 2013 | 4 | 4 & 6 | 3 | 4 | 0 | 0 |
| 2015 | 10 | 6 & 8 | 1 | 8 | 0 | 0 |
| 3002 | 5 | 4, 6, & 8 | 0 | 6 | 0 | 0 |
| 3005 | 1 | 8 | 3 | 6 | 0 | 0 |
| 3006 | 2 | 6 | 1 | 6 | 0 | 0 |
| 3008 | 0 | 4, 6, & 8 | 3 | 6 | 0 | 0 |
| 3009 | 3 | 8 | 0 | 6 | 0 | 0 |
| 4001 | 7 | 6 & 8 | 5 | 4 | 1 | 1 |
| 4005 | 2 | 6 | 2 | 4 & 6 | 1 | 0 |
| 4006 | 2 | 8 | 0 | 4 & 6 | 0 | 0 |
| 4007 | 3 | 4 & 6 | 0 | 6 | 1 | 0 |
| Total | 109 | | 25 | | 8 | 2 |
| Avg. | 4.74 | | 1.09 | | 0.35 | 0.09 |
| Mode | 2 | | 0 | | 0 | 0 |
| Median | 3 | | 0 | | 0 | 0 |
| Count | 23 | | 23 | | 23 | 23 |

During the dose escalation phase 109 drug related A.E.'s were reported, or an average of about 4.74 A.E.'s per patient. The findings for the constant dose phase reveal a total of 25 reported adverse events or about 1.1 A.E.'s per patient.

In all, 440 tablets were administered to the twenty-three patients exhibiting adverse events, as documented in Table XI, above, during the two phases combined—i.e., 157 four-milligram tablets, 176 six-milligram tablets, and 107 eight-milligram tablets. Sixty-nine of these tablets were administered in the in-patient phase (one tablet of each dosage to each patient). This leaves 371 tablets administered during the take-home phase. The remarkableness of the dose escalation data is highlighted when the number of A.E.'s per tablet between the two phases is compared, as shown in Table XII, below.

TABLE XII

Adverse Events per Tablet

| Phase | A.E.'s | Tablets taken | A.E./tablet |
|---|---|---|---|
| In-Patient | 109 | 69 | 1.58 |
| Take-Home | 25 | 371 | 0.07 |

The 0.07 adverse events per tablet during the take-home phase represents about a 95.6% decrease in adverse events per tablet over the in-patient phase. This dramatic improvement resulted from the dose escalation pretreatment.

Additionally, review of concomitant medications given to patients shows that a patient in the escalating dose or in-patient phase (Acclimation Treatment) of the study required an anti-emetic about 35% of the time (See Table XI above). In contrast, during the constant dose phase (Out-Patient Phase) the percentage of patients requiring anti-emetic medication dropped to approximately 9% (see FIG. 12). This sparing of concomitant medication for emesis further verifies the accelerated acclimatization of patients to apomorphine side effects by the dose escalation methodology.

A second aim of this study was to further test the efficacy of APO. This aim was accomplished during the first two phases of the study in which subjects were attached to the RIGISCAN™ monitor. Subjects were initially treated with placebo, followed by APO 4, 6, and 8 mg. tablets with a placebo tablet randomly interspersed in the treatment.

There were highly significant effects of APO treatment compared to placebo—placebo 1 administered during phase I and placebo II randomly administered during phase II—to suggest an effect of this drug on penile function both in an erotic and neutral environment, as shown by Table XIII, below.

TABLE XIII

Total RIGISCAN ™ Scores by Sequence (Erotic vs. Neutral)

| Sequence | Placebo 1 | Placebo 2 | 4 mg | 6 mg | 8 mg |
|---|---|---|---|---|---|
| Erotic 1 N = 31–36 | 11.44 ± 1.77 | 13.38 ± 2.05 | 15.31 ± 1.76* | 17.09 ± 1.64** | 19.84 ± 1.61** |
| Erotic 2 N = 29–36 | 11.39 ± 1.70 | 13.31 ± 1.88 | 15.26 ± 1.72* | 16.44 ± 1.98* | 17.79 ± 1.96** |
| Neutral N = 41–48 | 7.98 ± 1.24 | 7.49 ± 1.30 | 11.11 ± 1.30** | 12.76 ± 1.12** | 11.95 ± 1.37** |
| Corresponding p-values (placebo 1/placebo 2) | | | | | |
| Erotic 1 | — | 0.3274 | 0.0120 | 0.0007 | |
| | — | — | 0.1405 | 0.0166 | |
| Erotic 2 | — | 0.4013 | 0.0276 | 0.0196 | |
| | — | — | 0.1907 | 0.1365 | |
| Neutral | — | 0.6243 | 0.0230 | 0.0009 | |
| | — | — | 0.0074 | 0.0002 | |

*Significantly higher than placebo 1
**Significantly higher than placebo ± and placebo 2

Similarly, referring to Tables XIV and XIVb below and FIG. 14, the active doses of APO improved significantly the RIGISCAN™ scores for penile increases at each of the four sites in both the neutral and erotic sequences the only exception being a slightly lower erotic #1 RIGISCAN™ score at 4 mg for Site #1 (test results for the erotic video sequence at test site #3 are not available because these sequences were not shown to the subjects).

TABLE XIVa

Penile Measurements (Maximum increase) Measured by RIGISCAN ™
Intent-to-Treat Population
EROTIC #1 Video Sequence

| Site | Treatment | N | Mean | SEM | LSMEAN | SEM | Source | p-value |
|---|---|---|---|---|---|---|---|---|
| ALL SITES | Placebo #1 | 36 | 11.44 | 1.770 | 12.22 | 1.666 | Treatment | 0.0001 |
| | Placebo #2 | 32 | 13.38 | 2.051 | 13.65 | 1.714 | Site | 0.0264 |
| | 4 mg | 35 | 15.31 | 1.761 | 15.80 | 1.674 | Treatment by Site | 0.0595 |
| | 6 mg | 34 | 17.09 | 1.841 | 17.20 | 1.695 | 4 mg vs Placebo #1 | 0.0120 |
| | 8 mg | 31 | 19.84 | 1.610 | 19.11 | 1.745 | 6 mg vs Placebo #1 | 0.0007 |
| | | | | | | | 8 mg vs Placebo #1 | 0.0001 |
| #1 | All Treatments | 11 | 10.76 | 2.372 | 11.04 | 2.498 | 4 mg vs Placebo #2 | 0.1405 |
| | Placebo #1 | 11 | 9.73 | 2.854 | 9.73 | 2.931 | 6 mg vs Placebo #2 | 0.0166 |
| | Placebo #2 | 10 | 9.00 | 3.300 | 9.21 | 2.996 | 8 mg vs Placebo #2 | 0.0005 |
| | 4 mg | 11 | 8.09 | 2.410 | 8.09 | 2.931 | Placebo #1 vs #2 | 0.3274 |
| | 6 mg | 11 | 10.82 | 3.065 | 10.82 | 2.931 | | |
| | 8 mg | 9 | 17.89 | 2.988 | 17.36 | 3.070 | | |
| #2 | All Treatments | 16 | 13.89 | 1.942 | 14.25 | 2.083 | | |
| | Placebo #1 | 16 | 8.94 | 2.233 | 8.94 | 2.430 | | |
| | Placebo #2 | 14 | 11.71 | 2.768 | 11.38 | 2.515 | | |
| | 4 mg | 15 | 15.27 | 2.379 | 15.10 | 2.476 | | |
| | 6 mg | 15 | 17.60 | 2.267 | 17.43 | 2.476 | | |
| | 8 mg | 15 | 15.60 | 2.265 | 18.43 | 2.476 | | |
| #4 | All Treatment | 9 | 21.21 | 3.437 | 21.49 | 2.776 | | |
| | Placebo #1 | 9 | 18.00 | 4.304 | 18.00 | 3.240 | | |
| | Placebo #2 | 8 | 21.75 | 4.242 | 20.36 | 3.337 | | |

TABLE XIVa-continued

Penile Measurements (Maximum increase) Measured by RIGISCAN ™
Intent-to-Treat Population
EROTIC #1 Video Sequence

| Site | Treatment | N | Mean | SEM | LSMEAN | SEM | Source | p-value |
|---|---|---|---|---|---|---|---|---|
| | 4 mg | 9 | 24.22 | 2.827 | 24.22 | 3.240 | | |
| | 6 mg | 8 | 24.75 | 3.740 | 23.36 | 3.337 | | |
| | 8 mg | 7 | 25.00 | 3.259 | 21.52 | 3.444 | | |

TABLE XIVb

Penile Measurements (Maximum Increases Measured by Rigiscan)
Intent-to-Treat Population NEUTRAL Video Sequence

| | | | DESCRIPTIVE STATISTICS | | ADJUSTED (LS) MEAN | |
|---|---|---|---|---|---|---|
| Site | Treatment | N | MEAN | SEM | LSMEAN | SEM |
| ALL SITES | Placebo #1 | 48 | 7.98 | 1.236 | 8.34 | 1.220 |
| | Placebo #2 | 43 | 7.49 | 1.257 | 7.65 | 1.272 |
| | 4 mg | 47 | 11.11 | 1.295 | 11.47 | 1.226 |
| | 6 mg | 45 | 12.76 | 1.116 | 13.10 | 1.268 |
| | 8 mg | 41 | 11.98 | 1.366 | 12.40 | 1.331 |
| #1 | All Treatments | 11 | 10.56 | 1.987 | 10.70 | 1.789 |
| | Placebo #1 | 11 | 8.91 | 2.470 | 8.91 | 2.494 |
| | Placebo #2 | 10 | 5.60 | 2.574 | 5.68 | 2.587 |
| | 4 mg | 11 | 10.45 | 1.965 | 10.45 | 2.494 |
| | 6 mg | 11 | 12.73 | 2.832 | 12.73 | 2.494 |
| | 8 mg | 9 | 16.22 | 3.099 | 15.73 | 2.692 |
| #2 | All Treatments | 16 | 7.02 | 1.192 | 7.22 | 1.495 |
| | Placebo #1 | 16 | 4.44 | 1.554 | 4.44 | 2.068 |
| | Placebo #2 | 14 | 5.86 | 2.099 | 5.71 | 2.182 |
| | 4 mg | 15 | 8.73 | 2.610 | 8.70 | 2.126 |
| | 6 mg | 15 | 9.60 | 1.514 | 9.56 | 2.126 |
| | 8 mg | 15 | 7.73 | 1.694 | 7.70 | 2.126 |
| #3 | All Treatments | 12 | 12.22 | 1.476 | 12.09 | 1.706 |
| | Placebo #1 | 12 | 11.33 | 2.244 | 11.33 | 2.388 |
| | Placebo #2 | 11 | 10.00 | 1.902 | 10.61 | 2.469 |
| | 4 mg | 12 | 11.83 | 2.564 | 11.83 | 2.388 |
| | 6 mg | 12 | 13.58 | 1.794 | 13.58 | 2.388 |
| | 8 mg | 11 | 12.45 | 2.458 | 13.07 | 2.469 |
| #4 | All Treatments | 9 | 11.63 | 2.864 | 12.35 | 2.023 |
| | Placebo #1 | 9 | 8.67 | 4.052 | 8.67 | 2.758 |
| | Placebo #2 | 8 | 9.25 | 3.990 | 8.58 | 2.891 |
| | 4 mg | 9 | 14.89 | 3.071 | 14.89 | 2.758 |
| | 6 mg | 7 | 18.14 | 2.747 | 16.51 | 3.046 |
| | 8 mg | 6 | 15.33 | 4.462 | 13.11 | 3.236 |

INFERENTIAL STATISTICS

| Source | p-value |
|---|---|
| Treatment | 0.0002 |
| Site | 0.1092 |
| Treatment by Site | 0.7176 |
| 4 mg vs Placebo #1 | 0.0230 |
| 6 mg vs Placebo #1 | 0.0009 |
| 8 mg vs Placebo #1 | 0.0060 |
| 4 mg vs Placebo #2 | 0.0074 |
| 6 mg vs Placebo #2 | 0.0002 |
| 8 mg vs Placebo #2 | 0.0017 |
| Placebo #1 vs. #2 | 0.6243 |

The effects were seen especially in measurements conducted at the base of the penis, although all summed scores showed significant treatment effects at one or more of the three doses of APO. The above-referenced Tables and FIG. 14 show the overall RIGISCAN™ score results were significant to highly significant for a treatment effect of 4, 6, and 8 mg. compared to the initial placebo. In addition, most of the treatment effects were significant to highly significant compared to the second placebo. While the first and second placebo did not differ statistically, the results in the second were numerically higher.

Figure 14:
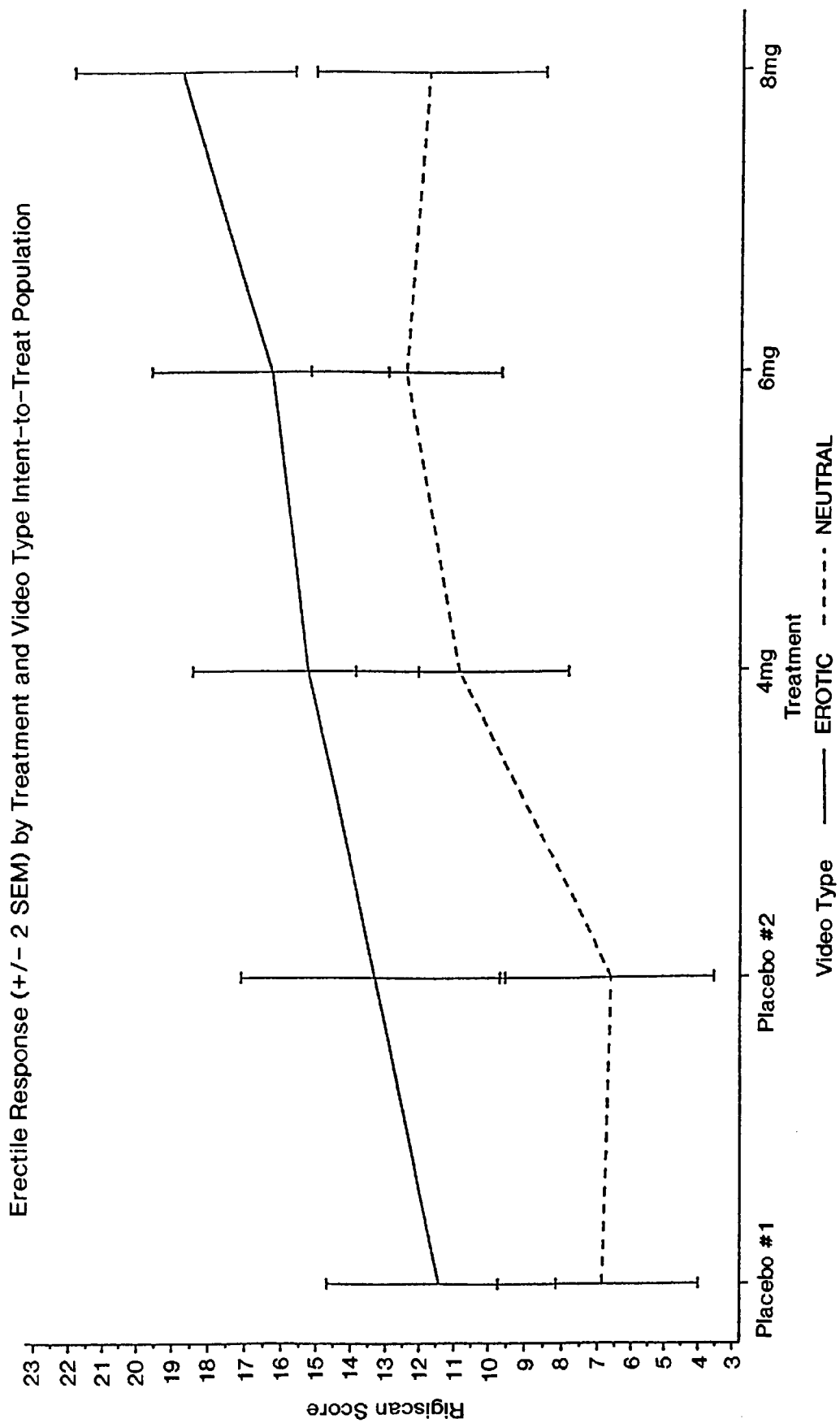
FIG. 14 is a line graph representing the mean RIGISCAN™ score for human participants at each dosing level and for each video type (i.e., erotic and neutral)

The results in the erotic phases were higher than those in the neutral phase and erotic one was numerically higher than erotic two (see FIG. 14). More significant treatment effects were seen in the neutral phase, but this reflects the larger number of subjects in this phase, as test center #3 (Columbia) did not air the erotic videos. All doses of APO were effective in causing erections (RIGISCAN™ readings greater than or equal to 15) in the presence of erotic stimulation.

For the third phase, subjects had recorded at baseline, their satisfaction, erection, number of attempts, and successful intercourse on a VAS scale (see Tables Xa–Xc, above). Evaluateable subjects first recorded a success rate, then completed VAS for erection results and satisfaction with intercourse following take-home treatment. The success rates, as shown in Tables XVa–XVb, below, were calculated for milligrams of APO as well as for micrograms per kilogram of the patient's body weight doses (males). There were four criteria for recording a success in the take-home phase. The criteria were: 1) subjects must have at least one of two successful intercourse attempts (based on subject's answers to the take-home questionnaires); 2) subjects must have tried the study medication at home, for at least two attempts; 3) subjects must have attempted to try a lower or higher dose if the original take-home dose did not produce optimum results in combination with anti-nausea agents; and 4) subjects [and partners] must have filled out and returned the take-home questionnaires. Several evaluations of the data were made including the male and female responses to treatments via questionnaires (see FIGS. 15 and 16).

TABLE XVa

Sexual Intercourse Success Rate by Tablet Dose

| Group | 4 mg | 6 mg | 8 mg | Overall |
|---|---|---|---|---|
| Female | 5/7 (71.4%) | 11/15 (73.3%) | 4/7 (57.1%) | 20/29 (70.0%) |
| Male | 5/7 (71.4%) | 11/15 (73.3%) | 4/7 (57.1%) | 20/29 (70.0%) |

TABLE XVb

Sexual Intercourse Success Rate by $\mu$g/kg body weight

| Group | 35–50 $\mu$g/kg | 50–74 $\mu$g/kg | >74 $\mu$g/kg | Overall |
|---|---|---|---|---|
| Female | 3/5 (60.0%) | 9/11 (81.8%) | 8/13 (61.5%) | 20/29 (70.0%) |
| Male | 4/5 (80.0%) | 8/11 (72.7%) | 8/13 (61.5%) | 20/29 (70.0%) |

The overall success rate for the study was 70% with APO treatment, as shown in the above tables, which is statistically greater than the baseline rate of 28%. The success rate showed numerical increases from four milligrams to six milligrams for male and female participants, but a decrease at eight milligrams for each group. The highest success rate, as shown by Table IVa was 73% in both males and females at six milligrams. However, a dose range of 50 to 74 μg/kg gave the highest success rate of 82% in females and 73% in males, as shown in Table XVb. The success rate by testing site is shown in Table XVI, below.

TABLE XVI

TAKE-HOME SUCCESS RATE SUMMARY

| Site | Evaluable Subjects | Take-Home Success | Take-Home Failure |
|---|---|---|---|
| #1 Kingston General Hospital Jeremy Heaton, M.D. | 9 | 7 | 2 |
| #2 Royal Victoria Hospital Magdy Hassouna, M.D. | 4* | 2 | 1 |
| #3 Columbia Presbyterian Medical Center Ridwan Shabsigh, M.D. | 9 | 8 | 1 |
| #4 University of Calfornia at San Francisco Emil Tanagho, M.D. | 7 | 3 | 4 |
| TOTAL | 29 | 20 | 8 |
|  |  | 72% Overall Success Rate |  |

*Eight subjects were non-evaluateable for various protocol violations

Tables XVIIa—XVIId, below, show the statistical results of phase III with respect to Rigiscan™ results (a and b) and intercourse satisfaction (c and d) based on question 1 and question 3, respectively, from the completed questionnaires (see FIGS. 15 and 16). These scores for erection rigidity (question 1) showed numerical improvement from baseline with the best results seen at 4 mg in males and 8 mg in females. The maximum improvement from baseline were 56% in males and 59% in females. The mean improvement were 29% in males and 34% in females. The VAS for satisfaction (question 3) showed similar results with a maximum improvement from baseline of 62% in females and 57% in males, both at 8 mg. The mean improvements were 34% in females and 45% in males.

TABLE XVIIa

Phase III Erection Results (Maximum) Percent Change from Baseline Efficacy Population
Sex: MALE

| Site | Treatment | DESCRIPTIVE STATISTICS | | | ADJUSTED (LS) MEAN LSMEAN | |
|---|---|---|---|---|---|---|
| | | N | MEAN(%) | SEM | (%) | SEM |
| All Sites | 4 mg | 7 | 55.71 | 15.055 | 55.71 | 14.058 |
| | 6 mg | 15 | 42.80 | 8.777 | 42.80 | 9.603 |
| | 8 mg | 7 | 31.86 | 15.636 | 31.86 | 14.058 |
| #1 | All | 9 | 52.22 | 12.986 | | |
| | 4 mg | 2 | 80.50 | 3.500 | | |
| | 6 mg | 5 | 34.20 | 19.405 | | |
| | 8 mg | 2 | 69.00 | 20.000 | | |
| #2 | All | 4 | 57.00 | 19.429 | | |
| | 4 mg | 1 | 71.00 | | | |
| | 6 mg | 2 | 79.00 | 1.000 | | |
| | 8 mg | 1 | -1.00 | | | |

TABLE XVIIa-continued

Phase III Erection Results (Maximum) Percent Change from Baseline Efficacy Population
Sex: MALE

| #3 | All | 9 | 36.22 | 11.236 |
|---|---|---|---|---|
| | 4 mg | 2 | 17.50 | 34.500 |
| | 6 mg | 4 | 46.75 | 14.250 |
| | 8 mg | 3 | 34.67 | 22.806 |
| #4 | All | 7 | 33.00 | 15.074 |
| | 4 mg | 1 | 61.50 | 36.500 |
| | 6 mg | 4 | 31.50 | 14.846 |
| | 8 mg | 1 | -18.0 | |

INFERENTIAL STATISTICS

| Source | p-value |
|---|---|
| Treatment | 0.4950 |

TABLE XVIIb

Phase III Erection Results (Maximum) Percent Change from Baseline Efficacy Population
Sex: FEMALE

| Site | Treatment | DESCRIPTIVE STATISTICS | | | ADJUSTED (LS) MEAN LSMEAN | |
|---|---|---|---|---|---|---|
| | | N | MEAN(%) | SEM | (%) | SEM |
| All Sites | 4 mg | 7 | 33.57 | 14.560 | 33.57 | 13.468 |
| | 6 mg | 15 | 45.00 | 9.103 | 45.00 | 9.201 |
| | 8 mg | 6 | 59.00 | 13.466 | 59.00 | 14.547 |
| #1 | All | 9 | 52.56 | 12.586 | | |
| | 4 mg | 2 | 78.50 | 4.500 | | |
| | 6 mg | 5 | 36.00 | 19.396 | | |
| | 8 mg | 2 | 68.00 | 18.000 | | |
| #2 | All | 4 | 41.25 | 23.708 | | |
| | 4 mg | 1 | -6.00 | | | |
| | 6 mg | 2 | 82.00 | 3.000 | | |
| | 8 mg | 1 | 7.00 | | | |
| #3 | All | 8 | 46.50 | 12.211 | | |
| | 4 mg | 2 | 18.00 | 36.000 | | |
| | 6 mg | 4 | 42.50 | 8.302 | | |
| | 8 mg | 2 | 83.00 | 17.000 | | |
| #4 | All | 7 | 36.29 | 12.163 | | |
| | 4 mg | 2 | 24.00 | 0.000 | | |
| | 6 mg | 4 | 40.25 | 21.933 | | |
| | 8 mg | 1 | 45.00 | | | |

INFERENTIAL STATISTICS

| Source | p-value |
|---|---|
| Treatment | 0.4507 |

TABLE XVIIc

Phase III Satisfaction Percent Change from Baseline Efficacy Population
Sex: MALE

| Site | Treatment | DESCRIPTIVE STATISTICS | | | ADJUSTED LSMEAN | (LS) MEAN |
|---|---|---|---|---|---|---|
| | | N | MEAN (%) | SEM | (%) | SEM |
| All Sites | 4 mg | 7 | 49.14 | 10.276 | 49.14 | 10.617 |
| | 6 mg | 15 | 51.47 | 6.373 | 51.47 | 7.253 |
| | 8 mg | 7 | 56.57 | 13.409 | 56.57 | 10.617 |
| #1 | All | 9 | 58.00 | 9.876 | | |
| | 4 mg | 2 | 67.50 | 14.500 | | |

TABLE XVIIc-continued

Phase III Satisfaction Percent Change from Baseline Efficacy Population
Sex: MALE

| Site | Treatment | DESCRIPTIVE STATISTICS | | ADJUSTED LSMEAN | (LS) MEAN |
|---|---|---|---|---|---|
| | | N | MEAN (%) | SEM | (%) | SEM |
| | 6 mg | 5 | 40.60 | 11.374 | | |
| | 8 mg | 2 | 92.00 | 2.000 | | |
| #2 | All | 4 | 48.50 | 15.387 | | |
| | 4 mg | 1 | 71.00 | | | |
| | 6 mg | 2 | 59.50 | 7.500 | | |
| | 8 mg | 1 | 4.00 | | | |
| #3 | All | 9 | 49.56 | 8.026 | | |
| | 4 mg | 2 | 34.50 | 8.500 | | |
| | 6 mg | 4 | 54.50 | 12.017 | | |
| | 8 mg | 3 | 53.00 | 19.035 | | |
| #4 | All | 7 | 50.00 | 11.719 | | |
| | 4 mg | 2 | 34.50 | 30.500 | | |
| | 6 mg | 4 | 58.00 | 16.253 | | |
| | 8 mg | 1 | 49.00 | | | |

---INFERENTIAL STATISTICS---

| Source | p-value |
|---|---|
| Treatment | 0.8776 |

TABLE XVIId

Phase III Satisfaction (Maximum) Change from Baseline Efficacy Population
Sex: FEMALE

| Site | Treatment | DESCRIPTIVE STATISTICS | | ADJUSTED LSMEAN | (LS) MEAN SEM |
|---|---|---|---|---|---|
| | | N | MEAN | SEM | | |
| All Sites | 4 mg | 7 | 41.86 | 14.626 | 41.86 | 13.535 |
| | 6 mg | 15 | 40.60 | 9.109 | 40.60 | 9.246 |
| | 8 mg | 6 | 62.33 | 13.723 | 62.33 | 14.619 |
| #1 | All | 9 | 57.00 | 16.058 | | |
| | 4 mg | 2 | 81.00 | 9.000 | | |
| | 6 mg | 5 | 33.00 | 24.251 | | |
| | 8 mg | 2 | 93.00 | 3.000 | | |
| #2 | All | 4 | 57.00 | 13.988 | | |
| | 4 mg | 1 | 72.00 | | | |
| | 6 mg | 2 | 68.00 | 16.000 | | |
| | 8 mg | 1 | 20.00 | | | |
| #3 | All | 8 | 37.75 | 9.599 | | |
| | 4 mg | 2 | 16.50 | 20.500 | | |
| | 6 mg | 4 | 30.50 | 7.354 | | |
| | 8 mg | 2 | 73.50 | 0.500 | | |
| #4 | All | 7 | 33.29 | 10.794 | | |
| | 4 mg | 2 | 13.00 | 23.000 | | |
| | 6 mg | 4 | 46.50 | 13.426 | | |
| | 8 mg | 1 | 21.00 | | | |

---INFERENTIAL STATISTICS---

| Source | p-value |
|---|---|
| Treatment | 0.4437 |

The foregoing discussion and the accompanying examples are presented as illustrative, and are not to be taken as limiting. Still other variations within the spirit and scope of this invention are possible and will readily present themselves to those skilled in the art.

We claim:

1. A method of minimizing adverse effects of apomorphine on a human patient comprising the steps of:
   (a) administering to a human patient a threshold dose of about 2 to about 8 mg of apomorphine;
   (b) administering to the human patient a series of increasing periodic doses of apomorphine greater than the threshold dose until a final apomorphine dose in excess of a therapeutic dose has been received by the human patient; and thereafter
   (c) administering to the human patient a therapeutic dose of apomorphine.

2. The method of claim 1 wherein the step of administering a series of increasing doses occurs at a rate of one dose per day for at least two days.

3. The method of claim 1 wherein the therapeutic dose of apomorphine is an amount sufficient to induce a penile erection sufficient for vaginal penetration.

4. The method of claim 1 wherein the therapeutic dose of apomorphine is an amount sufficient to ameliorate sexual dysfunction in a female patient by inducing clitoral erectogenesis and vaginal engorgement on stimulation of the female patient.

5. The method of claim 1 wherein the apomorphine is administered as a suppository.

6. The method of claim 1 wherein the apomorphine is administered transdermally.

7. The method of claim 1 wherein the apomorphine is administered by subcutaneous injection.

8. A method of minimizing adverse effects of apomorphine on a male patient comprising the steps of:
   (a) administering to the male patient a sublingual threshold dose of apomorphine;
   (b) administering to the male patient a series of increasing sublingual doses of apomorphine greater than the threshold dose until a final sublingual apomorphine dose in excess of that needed to produce a penile erection sufficient for penetration has been received by the male patient; and
   (c) administering to the male patient, prior to sexual activity, a sublingual therapeutic dose of apomorphine less than the final dose but sufficient to produce an erection adequate for penetration without attendant substantial adverse effects.

9. The method of claim 8 wherein the step of administering a series of increasing doses occurs at a rate of one dose per day for at least three days.

10. The method of claim 8 further comprising the step of maintaining an apomorphine concentration in the male patient's plasma within the range of about 0.3 to about 5.5 nanograms per milliliter during sexual activity.

11. The method of claim 8 further comprising the step of maintaining an apomorphine concentration in the male patient's plasma preferably within the range of about 0.3 to about 4 nanograms per milliliter during sexual activity.

12. The method of claim 8 further comprising the step of maintaining an apomorphine concentration in the male patient's plasma within the range of about 1 to about 2 nanograms per milliliter during sexual activity.

13. The method of claim 8 wherein the sublingual threshold dose of apomorphine is in the range of about 2 mg to about 8 mg.

14. The method of claim 8 wherein the sublingual therapeutic dose is in the range of about 35 to about 74 micrograms per kilogram of patient's body weight.

15. The method of claim 8 wherein the final sublingual dose of apomorphine is within the range of about 8 to about 10 mg.

16. The method of claim 8 wherein the sublingual therapeutic dose is in the range of about 50 to about 74 micrograms per kilogram of patient's body weight.

17. A method for amelioration of social phobia of a human patient, comprising the steps of:

(a) administering to the human patient a threshold dose of apomorphine;

(b) administering to the human patient a series of increasing periodic doses of apomorphine greater than the threshold dose until a final apomorphine dose in excess of a therapeutic dose of apomorphine has been received by the human patient, the therapeutic dose being an amount sufficient to reduce symptoms of social phobia; and thereafter (c) administering to the human patient the therapeutic dose of apomorphine.

18. The method of claim 17 wherein the therapeutic dose is administered to provide a patient's plasma concentration of apomorphine of about 5 to about 8 nanograms per milliliter.

19. A method of minimizing adverse effects of apomorphine on a human patient comprising the steps of:

administering to the human patient a threshold dose of apomorphine;

administering to the human patient a series of increasing doses of apomorphine greater than the threshold dose until a final sublingual apomorphine dose in excess of that needed to ameliorate Parkinsonism symptoms has been received by the human patient; and thereafter administering to the human patient a therapeutic dose of apomorphine less than the final dose but sufficient to ameliorate Parkinsonism symptoms without attendant substantial adverse effects.

20. The method of claim 19 wherein the therapeutic dose of apomorphine is administered subcutaneously in the range of about 3 to about 8 milligrams.

21. The method of claim 19 wherein the therapeutic dose of 5 apomorphine is administered in a sublingual dosage form containing apomorphine in the range of about 10 to about 60 milligrams.

22. The method of claim 19 wherein the threshold dose of apomorphine is administered subcutaneously in a dosage form containing apomorphine in the range of about 1 to about 5 milligrams.

23. The method of claim 19 further comprising the step of maintaining an apomorphine concentration in the patient's plasma within the range of about 3 to about 20 nanograms per milliliter.

* * * * *

UNITED STATES PATENT AND TRADEMARK OFFICE
CERTIFICATE OF CORRECTION

PATENT NO. : 5,994,363
DATED : November 30, 1999
INVENTOR(S) : Ragab El-Rashidy et al.

It is certified that error appears in the above-identified patent and that said Letters Patent is hereby corrected as shown below:

Cols. 15-16, in TABLE Xb:
    2nd column, under heading "All Sites Combined", line 11, "35.3" should be -- 38.3 --.

Cols. 17-18, in TABLE Xc:
    2nd column, under heading "All Sites Combined", line 8, "(25.0%)" should be -- (28.0%) --;
    3rd column, under heading "Site 1", line 2, "5.955" should be -- 5.985 --;
    4th column, under heading "Site 2", line 2, "5.536" should be -- 8.836 --;
    4th column, under heading "Site 2", line 13, "(43.5%)" should be -- (43.8%) --;
    5th column, under heading "Site 3", line 15, "(25.6%)" should be -- (28.6%) --.

Cols. 21-22, in TABLE XIVa:
    4th column, under heading "Mean", line 17, "15.60" should be -- 18.60 --.

Signed and Sealed this

Thirtieth Day of January, 2001

Attest:

Q. TODD DICKINSON

*Attesting Officer*      *Director of Patents and Trademarks*